US011096990B2

(12) United States Patent
Bueche et al.

(10) Patent No.: US 11,096,990 B2
(45) Date of Patent: *Aug. 24, 2021

(54) LIQUID INSULIN FORMULATIONS AND METHODS RELATING THERETO

(71) Applicant: Aerami Therapeutics, Inc., Durham, NC (US)

(72) Inventors: Blaine Bueche, San Mateo, CA (US); Mei-Chang Kuo, Palo Alto, CA (US); John Patton, San Francisco, CA (US); Matthew Sander, San Francisco, CA (US)

(73) Assignee: AERAMI THERAPEUTICS, INC., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/168,186

(22) Filed: Oct. 23, 2018

(65) Prior Publication Data

US 2019/0160153 A1 May 30, 2019

Related U.S. Application Data

(63) Continuation of application No. 14/977,137, filed on Dec. 21, 2015, now abandoned.

(60) Provisional application No. 62/120,573, filed on Feb. 25, 2015.

(51) Int. Cl.
*A61K 38/28* (2006.01)
*A61K 9/00* (2006.01)

(52) U.S. Cl.
CPC ............ *A61K 38/28* (2013.01); *A61K 9/0073* (2013.01)

(58) Field of Classification Search
CPC .................................................... A61K 38/28
See application file for complete search history.

(56) References Cited

U.S. PATENT DOCUMENTS

| | | |
|---|---|---|
| 4,564,129 A | 1/1986 | Urban et al. |
| 5,164,740 A | 11/1992 | Ivri |
| 5,261,601 A | 11/1993 | Ross et al. |
| 5,586,550 A | 12/1996 | Ivri et al. |
| 5,758,637 A | 6/1998 | Ivri et al. |
| 5,915,378 A | 6/1999 | Lloyd et al. |
| 5,938,117 A | 8/1999 | Ivri |
| 6,014,970 A | 1/2000 | Ivri et al. |
| 6,085,740 A | 7/2000 | Ivri et al. |
| 6,131,567 A | 10/2000 | Gonda et al. |
| 6,205,999 B1 | 3/2001 | Ivri et al. |
| 6,211,144 B1 | 4/2001 | Havelund |
| 6,312,665 B1 | 11/2001 | Modi |
| 6,427,682 B1 | 8/2002 | Klimowicz et al. |
| 6,467,476 B1 | 10/2002 | Ivri et al. |
| 6,489,292 B1 | 12/2002 | Havelund et al. |
| 6,540,153 B1 | 4/2003 | Ivri |
| 6,540,154 B1 | 4/2003 | Ivri et al. |
| 6,629,646 B1 | 10/2003 | Ivri |
| 6,635,617 B1 | 10/2003 | Havelund |
| 6,640,804 B2 | 11/2003 | Ivri et al. |
| 6,755,189 B2 | 6/2004 | Ivri et al. |
| 6,814,071 B2 | 11/2004 | Klimowicz et al. |
| 6,921,020 B2 | 7/2005 | Ivri |
| 6,926,208 B2 | 8/2005 | Ivri |
| 6,978,941 B2 | 12/2005 | Litherland et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,083,112 B2 | 8/2006 | Ivri |
| 7,100,600 B2 | 9/2006 | Loeffler et al. |
| 7,108,197 B2 | 9/2006 | Ivri |
| 7,174,888 B2 | 2/2007 | Ivri et al. |
| 7,195,011 B2 | 3/2007 | Loeffler et al. |
| 7,387,996 B2 | 6/2008 | Langkjaer |
| 7,628,339 B2 | 12/2009 | Ivri et al. |
| 9,180,261 B2 | 11/2015 | Patton et al. |
| 9,801,950 B2 | 10/2017 | Kim et al. |
| 10,076,613 B2 | 9/2018 | Patton et al. |
| 2001/0037805 A1 | 11/2001 | Gonda et al. |
| 2003/0072740 A1 | 4/2003 | Milstein et al. |
| 2004/0045546 A1 | 3/2004 | Hirsh |
| 2004/0134494 A1 | 7/2004 | Papania et al. |
| 2006/0239930 A1 | 10/2006 | Lamche et al. |
| 2007/0163572 A1 | 7/2007 | Addington et al. |
| 2008/0029083 A1 | 2/2008 | Masado et al. |
| 2008/0233053 A1 | 9/2008 | Gross et al. |
| 2009/0099065 A1 | 4/2009 | Madsen et al. |
| 2009/0157037 A1 | 6/2009 | Iyer et al. |
| 2009/0236445 A1 | 9/2009 | Lintern |

(Continued)

FOREIGN PATENT DOCUMENTS

| | | |
|---|---|---|
| AU | 2011205444 B2 | 1/2011 |
| CN | 2461580 Y | 11/2001 |

(Continued)

OTHER PUBLICATIONS

Of Eriksson H., Biotechnology Techniques 12: 329-334, (1998).*
Bierczyńska-Krzysik, et al., "Investigation of asparagine deamidation in a SOD1-based biosynthetic human insulin precursor by MALDI-TOF mass spectrometry", ACTA APB Bichimica Polonica, regular paper, vol. 61, No. Feb. 2017, Feb. 2017, pp. 349-357, available online at: www.actabp.pl.
Zheng, et al., "Influence of pH, buffer species, and storage temperature on physicochemical stability of a humanized monoclonal antibody LA298", International Journal of Pharmaceutics, 208 (2006), Oct. 10, 2005, pp. 46-51, available online at: www.sciencedirect.com.

(Continued)

*Primary Examiner* — Gyan Chandra
(74) *Attorney, Agent, or Firm* — Kilpatrick Townsend & Stockton LLP

(57) ABSTRACT

Liquid formulations of insulin that contain physically and chemically stable insulin but do not contain preservatives or stabilizers are provided. The formulations also lack surfactants. The formulations are useful for various modes of delivery including pulmonary delivery.

14 Claims, 9 Drawing Sheets

(56) References Cited

U.S. PATENT DOCUMENTS

| | | |
|---|---|---|
| 2011/0017431 A1 | 1/2011 | Yang et al. |
| 2011/0168170 A1 | 7/2011 | Patton et al. |
| 2011/0168172 A1 | 7/2011 | Patton et al. |
| 2013/0269684 A1 | 10/2013 | Patton |
| 2013/0269694 A1 | 10/2013 | Patton et al. |
| 2014/0135682 A1 | 5/2014 | Frost et al. |
| 2014/0328943 A1 | 11/2014 | Havelund et al. |
| 2015/0352297 A1 | 12/2015 | Stedman et al. |
| 2015/0352301 A1 | 12/2015 | Stedman et al. |
| 2016/0001018 A1 | 1/2016 | Fink et al. |
| 2016/0001019 A1 | 1/2016 | Fink et al. |
| 2016/0129088 A1 | 5/2016 | Patton et al. |
| 2016/0243199 A1 | 8/2016 | Bueche et al. |

FOREIGN PATENT DOCUMENTS

| | | |
|---|---|---|
| CN | 102740911 | 9/2014 |
| EP | 2514412 | 10/2012 |
| EP | 2523712 B1 | 9/2015 |
| WO | 1995/24183 A1 | 9/1995 |
| WO | 2000/029013 | 5/2000 |
| WO | 03/030829 A2 | 4/2003 |
| WO | 2007/047948 A2 | 4/2007 |
| WO | 2009/111612 A1 | 9/2009 |
| WO | 2011/088071 | 7/2011 |
| WO | 2013/158352 A1 | 10/2013 |
| WO | 2013/158353 A1 | 10/2013 |
| WO | 2014/017847 | 1/2014 |
| WO | 2016/137569 | 9/2016 |

OTHER PUBLICATIONS

*Aradigm and Novo Nordisk Execute Further Restructuring of Partnership*, Aradigm Press Release (Jul. 5, 2006), http://investor.aradigm.com/releasedetail.cfm?ReleaseID=325263.
*Aradigm Regains Inhaled Insulin Program from Novo Nordisk*, GEN News Highlight (Oct. 9, 2008), http://www.genengnews.com/gen-news-highlights/aradigm-regains-inhaled-insulin-program-from-novo-nordisk/43253230/?kwrd=Aradigm.
Berchtold H. and Hilgenfeld R., 1999, "Binding of Phenol to R6 Insulin Hexamers," *Biopolymers* 51(2):165-172.
Brange J. et al., 1992, "Chemical stability of insulin: 1. Hydrolytic degradation during storage of pharmaceutical preparations," *Pharm. Res.* 9:715-726.
Brange J., et al., 1992, "Chemical stability of insulin: 2. Formation of higher molecular weight transformation products during storage of pharmaceutical insulin preparations," *Pharm. Res.* 9: 149-158.
Brange J., and Langkjaer L., 1992, "Chemical stability of insulin: 3. Influence of excipients, formulation, and pH," *Acta Pharm. Nord.* 4:149-158.
Brange J, 1992, "Chemical stability of insulin: 4. Kinetics and mechanisms of the chemical transformation in pharmaceutical formulation," *Acta Pharm. Nord.* 4:209-222.
Brange J. et al., 1992, "Chemical stability of insulin:5. Isolation, characterization and identification of insulin transformation products," *Acta Pharm. Nord.* 4:223-232.
Brange, et al. (1994) Stability of insulin: studies on the physical and chemical stability of insulin in pharmaceutical formulation (Kluwer Academic Publishers; Dordrecht, The Netherlands).
Brange and Havelund (1983) Properties of Insulin in Solution, In: Artificial Systems for Insulin Delivery (Brunetti, et al. eds., Raven Press, New York), pp. 83-88.
Brzovic, et al., 1994, "Structural Asymmetry and Half-Site Reactivity in the T to R Allosteric Transition of the Insulin Hexamer," *Biochemistry* 33(44):13057-13069.
Darrington, et al., 1994, "The Role of Intramolecular Nucleophilic Catalysis and the Effects of Self-Association on the Deamidation of Human Insulin at Low pH," *Pharm. Res.* 11(6):784-793.
Derewenda, et al., 1989, "Phenol stabilizes more helix in a new symmetrical zinc insulin hexamer," *Nature* 338 (6216): 594-596.
Derewenda, et al., 1989, "Molecular structure of insulin: the insulin monomer and its assembly," *British Medical Bulletin* 45(1):4-18.
"Insulin Human", USP Monographs: Insulin Human, US Pharmacopeia, USP29-NF24, p. 1135, Jan.-Dec. 2006. Retrieved from: http://www.pharmacopeia.cn/v29240/usp29nf24s0_m40600.html on Oct. 27, 2017, 3 pages.
"Insulin Human Injection", USP Monographs: Insulin Human, US Pharmacopeia, USP29-NF24, p. 1136, Jan.-Dec. 2006 Retrieved from: http://www.pharmacopeia.cn/v29240/usp29nf24s0_m40605.html on Oct. 27, 2017, 2 pages.
"Insulin Human", European Pharmacopoeia 5.0, Jan. 2005:0838, pp. 1800-1802, Jan. 2005.
Galloway, et al., 1981, "Factors Influencing the Absorption, Serum Insulin Concentration, and Blood Glucose Responses After Injections of Regular Insulin and Various Insulin Mixtures," *Diabetes Care* 4(3):366-376.
Kets, et al., "Citrate increases glass transition temperature of vitrified sucrose preparations", Elsevier, Cryobiology vol. 48, Issue 1 (Feb. 2004), pp. 45-54.
Kim, et al., 1992, "pH Dependent Conformational Changes in the T- and R-States of Insulin in Solution: Circular Dichroic Studies in the pH Range of 6 to 10," *Biochemical and Biophysical Research Communications* 186(2):1115-1120.
Liu, F., et al., "*Pulmonary Delivery of Free and Liposomal Insulin*," Pharmaceutical Research, vol. 10, Feb. 1, 1993, 5 pages.
*Novo Nordisk Assigns Inhaled Insulin Patent Portfolio to Aradigm Corporation*, Fierce Biotech (Oct. 9, 2008), http://www.fiercebiotech.com/press-releases/novo-nordisk-assigns-inhaled-insulin-patent-portfolio-aradigm-corporation.
*Novo Nordisk refocuses its activities within inhaled insulin and discontinues the development of AERx*, Fierce Biotech (Jan. 14, 2008), http://www.fiercebiotech.com/press-releases/novo-nordisk-refocuses-its-activities-within-inhaled-insulin-and-discontinues-develop.
Profit, Louise, 2005, "Exubera® (inhaled insulin): an evidence-based review of its effectiveness in the management of diabetes," *Core Medical Publishing*, Knutsford, UK, 1(2): pp. 89-101.
Sélam, J.-L., *Inhaled Insulin: Promises and Concerns*, Journal of Diabetes Science and Technology 2(2):311-315 (Mar. 2008).
Sluzky et al., 1992, "Mechanism of Insulin Aggregation and Stabilization in Agitated Aqueous Solutions," *Biotechnol. Bioeng.* 40:895-903.
Strickley, et al., 1997, "Solid-State Stability of Human Insulin II. Effects of Water on Reactive Intermediate Partitioning in Lyophiles from pH 2-5 Solutions: Stabilization against Covalent Dimer Formation," *Journal of Pharmaceutical Sciences* 86(6): 645-53.
USP Monograph: Insulin Human (USP29-NF24), Pharmacopeial Forum: vol. 31(5):pp. 2403-2407, Dec. 1, 2015.
White, et al., "EXUBERA®: Pharmaceutical Development of a Novel Product for Pulmonary Delivery of Insulin", Diabetes Technology & Therapeutics, vol. 7, Issue 6 (Dec. 2005), pp. 896-906.
PCT/US2015/067129 received an International Search Report and Written Opinion dated Feb. 26, 2016, all pages.
PCT/US2015/067129 received an International Preliminary Report on Patentability dated Sep. 8, 2017, all pages.

\* cited by examiner

Insulin Related Substances in Insulin Formulations Containing Various Buffering Agents Iso B3 in Insulin Formulations at pH 7.0-7.8

Insulin Related Substances in Insulin Formulations at pH 7.0-7.8

Potency of 300 U/mL and 900 U/mL Insulin Formulations

Insulin Related Substances in 300 U/mL and 900 U/mL Insulin Formulations

Iso B3 in 300 U/mL and 900 U/mL Insulin Formulations

HMWP in 300 U/mL and 900 U/mL Insulin Formulations

Insulin Solubilitity in Citrate and 0.39% Zinc, pH 7.0 - pH7.3 (Refrigerated)

Insulin Solubility in Citrate and 0.45% Zinc, pH 8.0-7.3 (Refrigerated)

Insolubility in Citrate and 0.51% Zinc, pH 7.0 – 7.3 (Refrigerated)

6mM Citrate Insulin Concentration vs. pH and Zinc

Potency of Shaken Insulin Formulations

Turbidity of Insulin Formulations

Potency of Preservative Free and Phenol-Containing Formulations

LIQUID INSULIN FORMULATIONS AND METHODS RELATING THERETO

CROSS REFERENCE TO RELATED APPLICATION

This application is a continuation of U.S. patent application Ser. No. 14/977,137, filed Dec. 21, 2015, which claims the benefit of U.S. Provisional Application No. 62/120,573, filed Feb. 25, 2015, the complete disclosures of which are herein incorporated by reference.

BACKGROUND

Diabetes mellitus is a metabolic disorder in which an individual's ability to moderate blood glucose levels in response to insulin is lost. Insulin is a hormone secreted by the pancreas into the blood that triggers cells to take up glucose. When the body cannot produce insulin, as occurs in type 1 diabetes, or is no longer responsive to insulin and/or produces less insulin, as occurs in type 2 diabetes, blood glucose levels rise. Complications from diabetes include increased risk of cardiovascular disease, neuropathy, nephropathy, retinopathy, foot damage, skin conditions, hearing impairment, and Alzheimer's disease. Treatment for type 1 diabetes involves insulin injections or the use of an insulin pump. Type 2 diabetes is also often treated with insulin injections or pumps.

The human insulin protein is composed of 51 amino acids and has a molecular weight of 5808 Da. The amino acid sequence is strongly conserved in invertebrates. While initially synthesized as a single polypeptide chain, it is cleaved to form an A-chain and a B-chain that are linked together by disulfide bonds. Insulin is produced and stored in the body as a zinc-stabilized inactive hexamer (a unit of six insulin molecules), while the active form is the monomer. Hexameric insulin is very stable, serving to keep the highly reactive insulin protected, yet readily available in the blood. Hexamer formation and disassociation reflect the following equilibria:

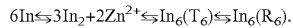

$6In \leftrightarrows 3In_2 + 2Zn^{2+} \leftrightarrows In_6(T_6) \leftrightarrows In_6(R_6)$.

Insulin monomers above 1 µm concentration can form non-covalent dimers ($In_2$). The binding of two zinc molecules facilitates 3 dimers ($In_2$) assembling into the hexameric form. Hexameric insulin can transition between two primary states: $T_6$ and $R_6$. The conversion between the T→R forms is related to the conformational flexibility in the N' terminal portion (B1-B8) of the B chain. In the T state, the B1-B8 region is in an extended linear state, while in the R state, it is an alpha helix. (Kim and Shield (1992) Biochem. Biophys. Res. Comm. 186(2): 1115-120.) The alpha helix form of the B1-B8 region can stabilize the hexamer. The interconversion between the $T_6$ and $R_6$ conformations of the insulin hexamer may be modulated by ligand binding to the $T_6$ and $R_6$ forms. Such ligands may include anions, preservatives, and stabilizers. For example, phenolic preservatives and stabilizers bind to hydrophobic pockets located near the surfaces of insulin to promote the $R_6$ state. (Derewenda et al. (1989) Nature 338(6216): 594-596; Brzovic et al. (1994) Biochemistry 33:13057-13069.)

Insulin degradation during storage is a challenge when developing commercial liquid insulin formulations. Insulin formulations degrade or lose potency by a number of physical processes and chemical reactions, including: a) precipitation (crystal formation); b) fibril formation (protein denaturation); c) hydrolysis reactions, especially deamidation of certain amino acid positions (including A18, A21 and B3); d) covalent dimerizations via transamidation or Schiff-base formation; and e) disulfide exchange reactions. (Strickley and Anderson (1997) J. Pharma. Sci. 86(6): 645-53.)

Fibril formation (aggregation) generally occurs when two or more partially unfolded insulin monomers are brought together by shaking or shear force (for example, during shipment). The hydrophobic surfaces of the insulin molecule bind together, irreversibly forming an insulin fiber. Insulin monomers continue to bind, and the fiber elongates until it becomes insoluble in aqueous solution. The formation of these inactive insulin fibers, results in visible cloudiness and loss of potency in insulin formulations.

Commercial insulin formulations often include the hexameric configuration of insulin and excipients such as preservatives or stabilizers (such as phenolic compounds), which contribute to the rigidity of the protein complex and promote hexamer stability. Conformational flexibility in the B1-B8 region of the B chain appears to be a factor in the chemical instability of insulin. An increase in the rigidity of the N' terminal B chain via increased interaction (promoting hexamer form), or by adding excipients (such as phenolic compounds) that induce a helical structure in the B1-B8 region, may decrease the deamidation and covalent dimer reactions (Berchtold and Hilgenfeld (1999) Biopolymers 51(2): 165-72; Derewenda et al. (1989) Nature 338(6216): 594-96; Darrington and Anderson (1994) Pharma. Res. 11(6): 784-793; Brange et al. (1994) Stability of insulin: studies on the physical and chemical stability of insulin in pharmaceutical formulation. Dordrecht, The Netherlands: Kluwer Academic Publishers.)

Phenolic compounds, in particular phenol and cresol, have proven so effective at stabilizing the B1 chain and promoting hexamer formation that they are routine components of commercial liquid insulin formulations. Many such preservatives and stabilizers can be mucose irritating and malodorous. However, formulations lacking such components (see, for example, U.S. Pat. No. 6,211,144) may have significant protein instability and may be more susceptible to physical instability during shipment.

BRIEF SUMMARY

Disclosed herein are liquid insulin formulations suitable containing insulin at a minimum concentration of 1-13 mM, a salt at a concentration of 50-150 mM, a pH buffering agent at a concentration of 3-24 mM, zinc at a ratio of 1.9-2.7 zinc ions per insulin hexamer (0.35-0.5% w/w zinc to insulin), and a pH in the range of 7.2 to 8.0. An important feature of these formulations is that they do not contain preservatives or stabilizers. Also provided are unit doses of such insulin formulations, and kit containing such formulations.

Further disclosed are methods of treating a subject with diabetes mellitus, the method involving administering to a subject having diabetes mellitus a therapeutically effective amount of an insulin formulation containing insulin at a minimum concentration of 1-13 mM, a salt at a concentration of 50-150 mM, a pH buffering agent at a concentration of 3-24 mM, zinc at a ratio of 1.9-2.7 zinc ions per insulin hexamer (0.35-0.5% w/w zinc to insulin), and a pH in the range of 7.2 to 8.0, wherein the formulation does not contain preservatives or stabilizers. The formulations may be administered to the subject via inhalation or injection.

It will be appreciated from a review of the remainder of this application that further methods and compositions are also part of the invention.

DETAILED DESCRIPTION

Figure 1:
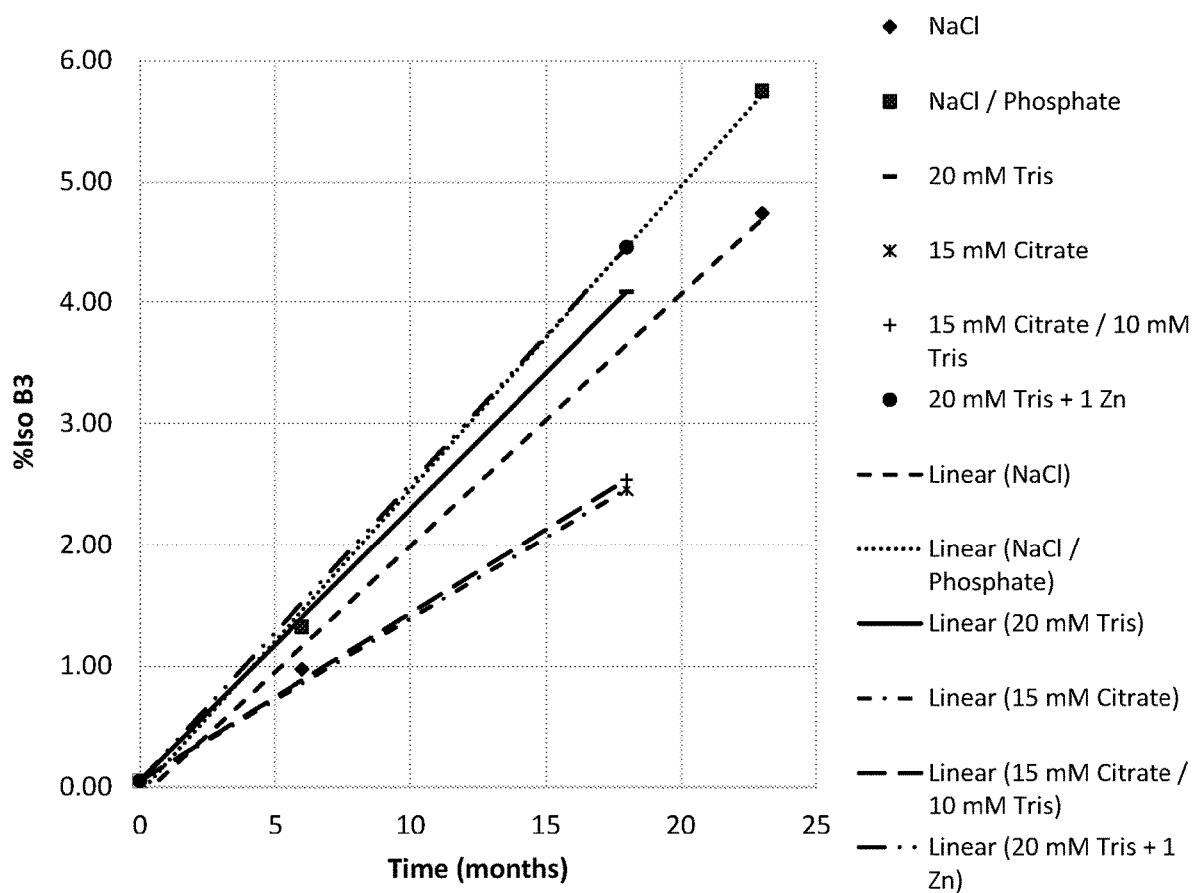
FIG. 1 shows the formation of Iso B3 insulin degradation product overtime in insulin formulations including different pH buffering agents (Phosphate, Tris, Citrate, Tris/Citrate) and/or salt (NaCl) according to some aspects.

This detailed description of the aspects and embodiments of the present disclosure is organized into sections as follows. Section I provides an introduction to the subject matter of the disclosure. Section II provides definitions of terms used herein. Section III describes the formulations. Section IV describes kits containing the formulations. Section V describes treatment methods. Section VI provides exemplary formulations and treatment methods. This detailed description is organized into sections only for the convenience of the reader, and disclosure found in any section is applicable to disclosure elsewhere in the specification.

I. Introduction

Certain embodiments and aspects of the present disclosure relate to liquid insulin formulations and methods of treating a subject having diabetes mellitus using the formulations. Relative to existing commercial formulations, the disclosed formulations are stable for sufficient periods of time for a viable commercial product. Importantly, the formulations are stable without containing preservatives or stabilizers, such as phenolic compounds. In addition, the described formulations have sufficient insulin concentration to be useful for delivering a desired dosage of insulin to a subject in a minimum volume, which can be particularly useful for pulmonary administration. In some instances, the formulations may contain relatively high insulin concentrations relative to commercial formulations. In some aspects, the formulations may be administered to a subject by aerosolization in a minimum volume and inhalation time. The formulations may be particularly suitable for aerosol delivery in part, by the lack of preservatives and stabilizers, which can be irritants and can impair dose delivery, by the lack of surfactants, which can also impair dose delivery, and by the relatively high insulin concentrations that can be provided. In addition, the formulations contain soluble insulin that is physically and chemically stable for extended periods of time even after extended exposure to shear forces. Long term stability, including chemical stability during storage and physical stability during shipping, handling, and patient use scenarios, is a factor in regulatory approval and commercial viability of an insulin formulation. The provided formulations may remain stable for an extended period of time such as, for example, at least 24 months, under appropriate storage conditions (refrigeration). Developing such insulin formulations, which are stable and may be relatively concentrated, required optimizing multiple factors and components to achieve a pH sufficiently high to maintain insulin solubility but sufficiently low to minimize chemical degradation (such as deamidation) and to maintain stability without the aid of preservatives or stabilizers as additives. The conditions identified for the formulations of this disclosure include a specific pH range and combination of components, including salt, zinc ions, and a pH buffering agent. An aspect of the formulations is that protein stability is controlled primarily through protein concentration, pH value, type of pH buffering agent, zinc ion concentration, and salt (ionic strength), without the need for chemical preservatives or stabilizers.

II. Definitions

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

"Administering" or "administration of" a formulation to a subject (and grammatical equivalents of this phrase), as used herein, refers to direct administration, which may be administration to a subject by a medical professional or may be self-administration, and/or indirect administration, which may be the act of prescribing a formulation. For example, a physician who instructs a subject to self-administer a formulation and/or provides a subject with a prescription for a formulation is administering the formulation to the subject.

"Chemical stability", as used herein, refers to the reactivity of a pharmaceutical composition in a pharmaceutical formulation and the propensity of the pharmaceutical composition to react chemically, or decompose chemically, in the pharmaceutical formulation. Examples of chemical instability for insulin formulations include oxidation and hydrolysis of the insulin protein.

"Physical stability", as used herein, refers to the ability of a pharmaceutical composition to retain its normal physical structure in a pharmaceutical formulation and, as a result, the propensity of the pharmaceutical composition to aggregate and/or precipitate out of solution during storage and usage. The physical stability of insulin formulations is reflected by the ability of the insulin protein to retain its native configuration in the formulation. Exemplary physical instability for insulin formulations includes fibrillation.

"Potency", as used herein, refers to the activity or amount of a active agent in a composition, such as the amount of insulin in a pharmaceutical formulation. Potency may be stated in terms of the amount of active agent required to produce an effect. For example, units of insulin per milliliter (U/mL), or milligrams of insulin per milliliter (mg/mL). As used herein, potency may be used to refer to the desired insulin concentration of the described formulations. In some instances, percent (%) potency may be used to refer to the amount of insulin (concentration) in a formulation as compared to a starting/initial concentration.

"Preservative", as used herein, refers to a class of compounds that prevents or inhibits the growth of microorganisms, as well as compounds that help control oxidation reactions in pharmaceuticals. Phenol and EDTA are examples of preservatives.

"Stabilizer", as used herein, refers to a substance that acts to stabilize secondary and tertiary structures of proteins in solution and, as a result, reduces the rate of degradation (chemical, physical, or both) of the proteins. For the insulin hexamer, exemplary stabilizers are phenol, meta-cresol, and other phenolic compounds.

"Surfactants", as used herein, refers to amphiphilic organic compounds (having hydrophobic groups and hydrophilic groups) that aggregate to form micelles in aqueous formulations at critical concentrations, providing greater solubility for hydrophobic compounds. Surfactants may be applied to formulations may increase the physical stability of the formulations, modify their solubility, or both.

"Therapeutically effective amount" of an insulin formulation, as used herein, refers to an amount of an insulin formulation that, when administered to a subject with diabetes mellitus, will have the intended therapeutic effect, for example, increased cellular uptake of blood glucose and reduced blood glucose levels. A therapeutically effective amount may be administered in one or more administrations.

"Treating" or "treatment of" a condition or subject, as used herein, refers to taking action to obtain beneficial or desired results, including clinical results, for a subject. For purposes of this disclosure, beneficial or desired clinical results include, but are not limited to, increased cellular uptake of blood glucose, reduced blood glucose levels, or both.

III. Formulations

Provided are stable insulin formulations that do not contain preservatives, stabilizers, or surfactants. The formulations may include 1-13 mM insulin, 50 to 150 mM of a salt, 3 to 24 mM of a buffering agent; zinc ions at a ratio of 1.9 to 2.7 zinc ions per insulin hexamer (alternatively referred to as 0.35% to 0.5% wt/wt of zinc to insulin), and a pH of 7.2 to 8.0. In some instances, the formulations may include 6 mg/mL to 76 mg/mL insulin.

Several properties of insulin were taken into account in the development of the formulations described herein. Development factored in that the self-association pattern of insulin in solution is a complex function of protein concentration, metal ions, pH, ionic strength, and solvent composition. In one aspect, the formulations include hexameric insulin as the majority insulin species. The formulations are generally formulated to minimize the formation of insulin degradation products.

In one aspect, the formulations contain insulin. In some instances, the formulations may contain insulin in the range of 1 mM to 13 mM. In some instances, the formulations may contain insulin in the range of 6 mg/mL to 76 mg/mL. In some instances, the formulations may contain insulin in the range of 173 U/mL to 2189 U/mL. For example, the formulations may have 1 mM, 2 mM, 3 mM, 4 mM, 5 mM, 6 mM, 7 mM, 8 mM, 9 mM, 10 mM, 11 mM, 12 mM, or 13 mM, or a concentration within 0.5 mM of any of these concentrations. In some instances, the formulations may have an insulin concentration of 6 mg/mL, 10 mg/mL, 15 mg/mL, 20 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, or a concentration with 3 m/mL of any of these concentrations. In some instances, the formulations may have an insulin concentration of about 170 U/ml, 175 U/ml, 190 U/ml, 225 U/ml, 260 U/ml, 280 U/ml, 300 U/ml, 325 U/ml, 350 U/ml, 375 U/ml, 400 U/ml, 425 U/ml, 450 U/ml, 475 U/ml, 500 U/ml, 525 U/ml, 550 U/ml, 600 U/ml, 625 U/ml, 650 U/ml, 675 U/ml, 700 U/ml, 725 U/ml, 750 U/ml, 775 U/ml, 800 U/ml, 825 U/ml, 850 U/ml, 875 U/ml, 900 U/ml, 925 U/ml, 950 U/ml, 975 U/ml, 1000 U/ml, 1025 U/ml, 1050 U/ml, 1075 U/ml, 1100 U/ml, 1125 U/ml, 1150 U/ml, 1175 U/ml, 1200 U/ml, 1225 U/ml, 1250 U/ml, 1275 U/ml, 1300 U/ml, 1325 U/ml, 1350 U/ml, 1375 U/ml, 1400 U/ml, 1425 U/ml, 1450 U/ml, 1475 U/ml, 1500 U/ml, 1525 U/ml, 1550 U/ml, 1575 U/ml, 1600 U/ml, 1625 U/ml, 1650 U/ml, 1675 U/ml, 1700 U/ml, 1725 U/ml, 1750 U/ml, 1775 U/ml, 1800 U/ml, 1825 U/ml, 1850 U/ml, 1875 U/ml, 1900 U/ml, 1925 U/ml, 1950 U/ml, 1975 U/ml, 2000 U/ml, 2025

U/ml, 2050 U/ml, 2075 U/ml, 2100 U/ml, 1225 U/ml, 1250 U/ml, 1275 U/ml, or 2200 U/ml. The formulations may contain an insulin concentration of at least 30 mg/mL or 5.17 mM. The formulations may contain an insulin concentration up to about 76 mg/mL or 13 mM. In some instances, the formulations may have an insulin concentration of 30 mg/mL to 76 mg/ml or 5.17 mM to 13 mM. In some instances, the formulations may have an insulin concentration of 10 mg/mL to 30 mg/ml or 1.72 mM to 5.17 mM. In certain aspects, the formulations may contain an insulin concentration in the range of 6 mg/mL to 35 mg/mL or 1 mM to 6.03 mM. In some instances, the formulations contain insulin that is primarily in a hexameric state, which can enhance chemical stability of insulin in the formulations. In some examples, the formulations may be 3 to 10 times more concentrated than existing commercial formulations. In some instances, the formulations may be up to 20 times more concentrated than existing commercial formulations such as, for example, Humulin® R U-100 (100 U/mL, 3.47 mg/ml), pH 7.4, and Humulin® R U-500 (500 U/mL, 17.35 mg/ml, 2.99 mM), pH 7.4 (Eli Lilly).

The type of insulin included in the formulations may vary. In some instances, the insulin may be human, porcine, or bovine insulin. In some instances, the formulation includes human insulin. In some instances, the insulin is human insulin. The insulin may be a recombinant protein derived from human or other mammalian cell lines. In some instances, the insulin may be a recombinant insulin protein derived from prokaryotic cells. In some instances, the insulin may be the full-length, 51 amino acid wild-type sequence of the insulin protein. In other instances, the insulin may be an insulin analogue that has a genetically modified sequence. For example, the insulin may have one or more amino acids deleted and/or replaced by other amino acids, including non-codeable amino acids, or may have one or more amino acids added to the protein sequence. In some instances, as described in Examples 1 to 6, the formulations may contain recombinant human insulin as commercially available from various suppliers (for example, Sanofi-Aventis (Material: 192228, GMID: 341921), EMD Millipore (Cat. #407709-50MG), Sigma Aldrich (CAS #11061-68-0, Cat. #91077C, EC #234-279-7, MDL #MFCD00131380)). For reference, 1 U is equivalent to 0.0347 mg of human insulin (28.8 U/mg). Also, as noted above, the molecular weight of human insulin is 5808 Daltons (g/mol).

In one aspect, the formulation may be isotonic. Extremely hypotonic or hypertonic solutions can cause mucus membrane irritation. For example, inhalation of low salt solutions (such as pure water) or high salt solutions can cause irritation of the throat and lungs, often resulting in coughing and discomfort. In some instances, the formulations have a tonicity of 100 mOsm-300 mOsm. Various compounds can be used to adjust the tonicity of the formulations. Tonicity of the formulations may be adjusted by including a salt or other solute that does not readily cross a cell membrane. In some instances, the salt concentration may be modified to optimize ionic strength and tonicity. In some instances, the concentration of the salt may be varied as the concentration of insulin in the formulation is varied to achieve the desired tonicity. In some instances, ionic strength of the formulations may be optimized to make the formulation comfortable to inhale (such as for pulmonary administration).

In some instances, the formulations may include a chloride salt. In some cases, the salt is a chloride salt. For example, in some instances, the salt may be sodium chloride. In some cases, insulin may be particularly stable in a formulation comprising sodium chloride as compared to other salts. For example, as described in Examples 1 to 6, the salt may be NaCl. In another aspect, the formulations may contain a salt, such as a chloride salt, in the range of about 50 to 150 mM. For example, the salt concentration may be about 50-70 mM, about 60-80 mM, about 90-100 mM, about 65-75 mM, about 75-85 mM, about 85-95 mM, about 70-140 mM, about 110-120 mM, about 130-150 mM, or any range therein. In some examples, the salt concentration may be about 50 mM, about 55 mM, about 60 mM, about 65 mM, about 70 mM, about 75 mM, about 80 mM, about 85 mM, about 90 mM, about 95 mM, about 100 mM, or a concentration within 2-3 mM of any of these concentrations. In some instances, as described in Examples 1 to 6, NaCl may be included in the formulations at a concentration of 70 mM.

In one aspect, the formulation contains 1.9 to 2.7 zinc ions per six molecules of insulin (hexamer), which is equivalent to about 0.35% to 0.5% wt/wt of zinc to insulin. In some instances, the zinc ions may promote the solubility of the insulin in the formulation. For example, two zinc ions may promote and/or stabilize the insulin hexamer. For example, in the absence of zinc ions, or if the zinc to hexamer ratio is too low (such as less that 1.9:1), the insulin may be physically unstable and unlikely to form hexamers. Also, for example, if the ratio of zinc ion to insulin hexamer is too high (such as 3:1 or greater), the insulin may precipitate out of solution. In some instances, 0.35% to 0.5% wt/wt of zinc to insulin provides stability to the insulin in formulation. In some instances, various proportions of the insulin in the provided formulations may be bound with 0, 1, 2, or 3 zinc ions, or a mixture thereof, such that the ratio of zinc ions to insulin hexamer for the formulation is 1.9 to 2.7. The formulations may contain 1.9, 2.0, 2.1, 2.2, 2.3, 2.4, 2.5, 2.6, or 2.7 zinc ions per insulin hexamer. In some instances, the formulations may contain 2.0 to 2.3 zinc ions per hexamer, 2.1 to 2.4 zinc ions per hexamer, 2.2 to 2.5 zinc ions per hexamers, 1.9 to 2.5 zinc ions per hexamer, 2.2 to 2.7 zinc ions per hexamer, 2.2 to 2.6 zinc ions per hexamer, or 2.3 to 2.6 zinc ions per hexamer.

In another aspect, the formulations may have a pH buffering capacity. For example, the formulations may include a pH buffering agent. For example, the pH buffering agent can be an ionizable salt such as phosphate, acetate, citrate, bicarbonate, Tris, and the like, with a counter-ion. The pH buffering agent acts to reduce fluctuations in the pH of the formulation. In certain instances, the pH buffering agent may be citrate, Tris, or Tris-citrate as described in Example 1 and shown in FIG. 1 and FIG. 2. In another aspect, the formulations may include a pH buffering agent at a concentration of about 3 to 24 mM. For example, the pH buffering agent concentration may be 3-6 mM, 5-10 mM, 8-16 mM, or 12-24 mM. In some instances, the pH buffering agent concentration may be 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, or 24 mM, or any concentration with 0.5 mM of these concentrations. In some instances, the pH buffering agent is citrate. In some instances, the pH buffering agent may be 6 mM citrate.

The stability and solubility of insulin may be influenced by the pH of the formulation. For example, the solubility of insulin is low at pH values near its isoelectric pH (pH range 4.0-7.0). In one aspect, the formulations may have a relatively neutral pH such as, for example, within 0.6 pH units of physiological pH (approximately 7.4). In some instances, the pH of the formulations may be slightly alkaline, such as up to pH 8. The pH of the formulations may be in the range of 7.2 to 8.0. A pH within this range, in combination with the components of the formulations, imparts particular stability to the insulin in the formulations. For example, the pH of the formulation may be about 7.2 to about 8.0. In some instances, the formulation has a pH of 7.2, 7.25, 7.3, 7.35, 7.4, 7.45, 7.5, 7.55, 7.6, 7.65, 7.7, 7.75, 7.8, 7.85, 7.9, 7.95, or 8.0, or a pH within 0.5 of any of these pH values. In some instances, the chemical and physical stability of formulations may be reduced at pH less than 7.2. In certain cases, the insulin protein may start to degrade at pH 8.0. Highly concentrated solutions of porcine insulin (5000 U/ml, approx. 30 mM) have been created at acidic pH but the insulin in the formulation is highly unstable due to deamidation. (Galloway (1981) Diabetes Care 4, 366-376.) Highly concentrated solutions of zinc-free insulin can be made at slightly alkaline pH (such as pH 8-9) but they are unstable due to a high rate of polymerization and deamidation. Also, highly concentrated porcine zinc insulin solutions at neutral pH comprising phenol are physically stable at elevated temperature but become supersaturated when the temperature is lowered to 4° C. (Brange and Havelund, Properties of Insulin in Solution, Artificial Systems for Insulin Delivery, 1983 (Brunetti et al. eds., Raven Press, New York), pp. 83-88.) In contrast, the formulations of this disclosure are stable and may contain concentrated insulin at a pH of 7.2 to 8.0 without including preservatives or stabilizers as described in Examples 1 to 6 and shown in FIGS. 1-15. In one example, as described in Example 3, formulations may have a pH of about 7.5 and include about 30 mg/mL insulin. In another example, as described in Example 3, formulations may have a pH of about 7.5 and include about 10 mg/mL insulin. In another example, as described in Example 4, the formulations may contain 35 mg/mL insulin at pH 7.2 and pH 7.3. In another example, as described in Example 5, the formulations may contain either 9.7 mg/mL or 29.2 mg/mL at pH 7.55. In another example, as described in Example 6, the formulations may contain 70 mg/mL insulin at either pH 7.2 and 7.4.

In some instances, the pH of the formulations may impact insulin degradation. As mentioned, two primary routes of insulin degradation are hydrolysis and the formation of high molecular weight polymers (HMWP). The most common hydrolysis products are B3 deamidated insulin (B3 and Iso B3) and A21 deamidated insulin (A21), arising from deamidation at the $3^{rd}$ amino acid (Asn) in the B chain and deamidation at the $21^{st}$ amino acid (Asn) in the A chain, respectively. In some instances, hydrolytic degradation of insulin having an aspargine at amino acid position 21 (A21) may be highest in acidic pH, lowest at a pH of 6.5, and generally low at neutral pH. In one example, the predominant hydrolysis product at low pH may be deamidation (loss of an ammonia group) from Asparagine A21 (A21-Asn). In another example, hydrolysis may increase at alkaline pH (such as pH 7.5-9.0) with deamidation generally occurring predominantly at Asparagine B3 (B3-Asn). In some instances, the deamidation of Asn-B3 may proceed via formation of a cyclic imide intermediate to form aspartic acid (B3) and iso-aspartic acid (Iso B3), producing two separate by-products. As A21, B3 and Iso B3 are nearly 100% bioactive (Brange et al. (1992) Acta Pharm. Nord. 4:223-232), these degradation products generally do not impair the potency of the insulin formulations.

The accumulation of HMWP products can be more problematic for the production of stable commercial insulin formulations, which are required to have very low amounts of such degradants for injectable insulin products (for example, 1.7% limit on HMWP; see U.S. Pharmacopeia (U.S. Monograph)). In some instances, maximum stability of aqueous insulin formulations may occur around neutral pH. In some cases, the rate of HMWP product formation of insulin may be high at acidic pH in many aqueous formulations but relatively low at pH in the range of about 6.5 to 8.0. For example, the rate of formation of HMWP products may be accelerated in alkaline media above pH 9.0 (for example, because disulfide reactions may be favored). Limiting HMWP formation is the reason nearly all commercial injectable insulin formulations are currently formulated at neutral pH. However, HMWP products may still form at neutral pH. Formation of these products mainly occurs by intermolecular aminolysis between N-terminal amines, especially between the B1-Asn and the amide side chains in the insulin A-chain of an adjacent insulin molecule, particularly within a hexamer.

In one aspect, the formulations do not contain preservatives or stabilizers. In some instances, preservatives and stabilizers are phenolic compounds. Examples of phenolic compounds include phenol, cresol, and derivatives thereof. In some instances, the formulations do not contain organic solvents. In certain aspects, the formulations do not contain alcohols, including polyols, sugars, amino acids, or amines. Formulations containing preservatives and stabilizers are described in U.S. Pat. Nos. 6,489,292 and 6,211,144, which are incorporated herein by reference. Such preservatives and stabilizers can include phenol and derivatives thereof such as meta-cresol, chloro-cresol, methylparaben, ethyl paraben, propyl paraben, thymol, as well as derivatives thereof and mixtures of such compounds. Some similar non-phenol preservatives and stabilizers include bi- or tricyclic aliphatic alcohols and purines, such as a bicyclic aliphatic alcohol, including a monoterpenol, such as isopinocampheol, 2,3-pinandiol, myrtanol, bomeol, norbomeol or fenchol, a tricyclic aliphatic alcohol, such as 1-adamantanol, and purines such as adenine, guanine or hypoxanthine. Other exemplary preservatives and stabilizers include sodium benzoate, benzalkonium chloride, benzyl alcohol, and thimerosal. Such preservatives and stabilizers are generally included to ensure stability of the insulin in formulations. In contrast, the formulations of the present disclosure maintain the stability of insulin in a concentrated form without including preservatives or stabilizers. In some instances, the formulations do not contain phenol, cresol, or derivatives of either. In some instances, as described in Table 12 and FIG. 15, 0.25% wt/vol phenol may decrease the stability of an insulin formulation as compared to a formulation as provided by this disclosure (preservative free) within a day of formulation and over a period of 6 months.

In another aspect, the formulations do not contain surfactants. For example, the formulations do not contain amphipathic excipients that modify the surface tension between a solution and any interface (for example, a liquid/glass vial interface, an air/liquid interface). Surfactants such as polysorbate-80 and Triton™ X-100 are well-known excipients. As surfactants may cause foaming and, therefore, loss of physical stability when a formulation is nebulized or aerosolized, the formulations provided by this disclosure provide an advantage over formulations containing surfactants.

As described in the Examples, the formulations provided in this disclosure are stable, with low levels of chemical and physical degradation, for at least 24 months at typical refrigeration temperatures (2-8° C., approx. 5° C.). As such, the formulation may be suitable for providing products with long shelf-stability.

Long term stability can be assessed by analysis of the physical and chemical properties of the formulations. For example, the physical appearance of the formulation may reveal the presence of precipitates, other insoluble components, and discoloring contaminants. Another example is that a change in the pH of the formulation may occur if stability decreases. Another example is that the potency of the formulation (the amount of soluble insulin) may decrease if stability decreases. Another example is the purity of the insulin in the formulation may decrease such as, for example, by an increase in the amount of desamido content (such as Iso B3 and A21 impurities), HMWP products (such as insulin dimers and polymers), and other insulin related substances (IRS). The term Insulin related substances (IRS) generally encompasses all insulin degradation products except A21, B3 and Iso B3 deamidated insulin. Specifications for commercial formulations are often established by pharmacopeial monographs, such as the USP Monograph: Insulin Human (USP29-NF 24, Pharmacopeial Forum:Vol. 31(5): 1135) and European Pharmacopeia: Insulin Human (01/2005:0838, pg. 1800-1801, Acta. Pharm. Nord. 223-232). These specifications are useful as guidelines for development of insulin inhalation solutions. For example, specifications for the stability of injectable insulin may be found in the European Pharmacopeia as set forth below and may be used as guidelines for a stable, commercially viable insulin inhalation formulation:

| Property | Guideline |
|---|---|
| Potency | 90-110% of target |
| High Molecular Weight Polymers (% HMWP) | ≤1.7% |
| Insulin Related Substances (% IRS) | ≤6% |

In some instances, the formulations may meet the requirements set forth in the table above for one or more of potency, % HWMP, or % IRS for at least 6 months, at least 12 months, at least 18 months, at least 24 months, or at least the duration of the shelf life of a commercial product comprising the formulations. In certain cases, the formulations may maintain relatively low levels of contaminants in the form of desamido products, HMWP products, or other IRS over time during storage. In some instances, the formulations provided may maintain relatively low levels of one or more of A21, Iso B3, and B3 insulin products over time during refrigerated storage. For example, as described in Examples 1-3, the amount of Iso B3 remained below 5% for the formulations provided by this disclosure for up to 23-24 months. These formulations also maintained IRS levels below 6% for up to 23-24 months. In another example, as described in Example 3, the provided formulations maintain an amount of A21 of less than 5% and an amount of HMWP of less than 1.7%.

Figure 2:
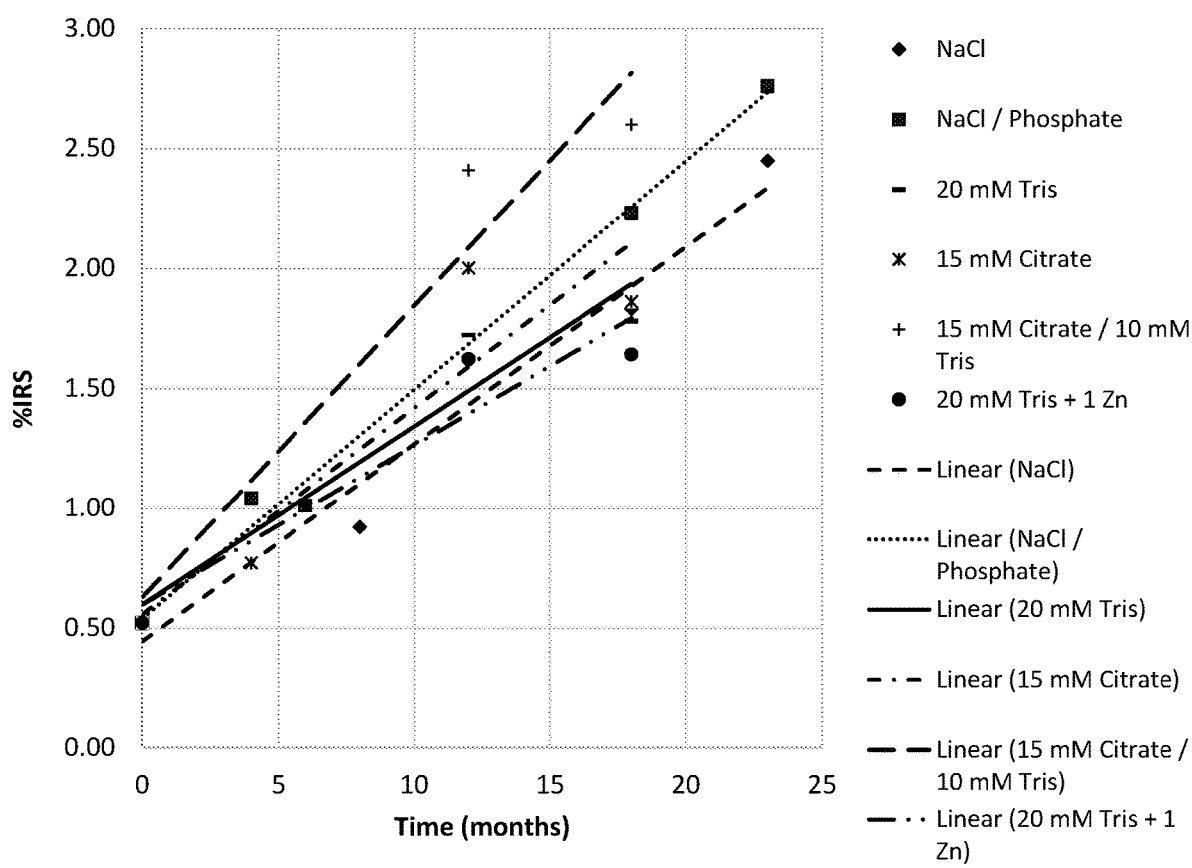
FIG. 2 shows the formation of Insulin Related Substances (IRS) degradation product overtime in the same insulin formulations as shown in FIG. 1 according to some aspects.

In some instances, the insulin formulations provided are chemically and physical stable. In some instances, stability is related to the pH buffering agent of the formulation. For example, as described in Table 2, the rate of Iso B3 formation may range from about 0.14-0.25% per month depending on the pH buffering agent. In some instances, as shown in FIG. 1, a pH buffering agent like citrate, or a Tris-citrate mixture, may result in only about 1% Iso B3 formation after 6 months and only about 2.5% after 18 months at typical refrigeration temperatures (2-8° C., approx. 5° C.). In some instances, other pH buffering agents like Tris or phosphate buffer alone, may result in only about 4.0-4.5% Iso B3 formation after 18 months and only about 4.5-5.9% after 24 months at typical refrigeration temperatures (2-8° C., approx. 5° C.). In some examples, the rate of IRS formation may range from about 0.11-0.12% per month for pH buffering agents such as citrate, Tris, and phosphate and may be about 0.16% per month for citrate-Tris mixture buffer, as described in Table 3. For example, as shown in FIG. 2, the a pH buffering agent like citrate, or a Tris-citrate mixture, may result in only about 1% IRS formation after 6 months, only about 1.8% after 18 months for a citrate buffer, or only about 2.5% after 18 months for a citrate-Tris buffer, at typical refrigeration temperatures (2-8° C., approx. 5° C.). In some instances, other pH buffering agents like Tris or phosphate buffer alone, may result in IRS formation at rates intermediate to those observed for citrate and Tris-citrate at typical refrigeration temperatures (2-8° C., approx. 5° C.). In some instances, the provided formulations may contain 31.2 mg/mL (900 U/mL) insulin and 70 mM NaCl with 0.42% w/w zinc to insulin (about 2.2 zinc per insulin hexamer) at pH 7.5 as described in Table 2, FIG. 1, and FIG. 2.

In some instances, chemical and physical stability of the formulations is related to pH. For example, as described in Example 2, the formation of Iso B3 may decrease, and the formation of IRS may increase, as the pH of the formulation increases and vice versa. In some instances, as shown in Table 4 and shown in FIG. 3, the rate of formation of Iso B3 at typical refrigeration temperatures may increase with increasing pH from 0.13% per month at pH 7.0 to 0.21% per month at pH 7.8. In contrast, as described in Table 5 and shown in FIG. 4, in some instances the rate of formation of IRS at typical refrigeration temperatures decreases with increasing pH from 0.21% per month at pH 7.0 to 0.09% per month at pH 7.8. In another example, the stability of the formulations decreases substantially under very basic conditions such as pH 8.7 when stored at typical room temperature (about 22 to 27° C.) as described in Table 6. In some instances, the formulations described in Tables 4 and 5 and FIGS. 3-4, may contain 31.2 mg/mL (900 U/mL) insulin, 6 mM citrate, and 70 mM NaCl, with 0.42% w/w zinc to insulin (about 2.2 zinc per insulin hexamer).

Figure 5:
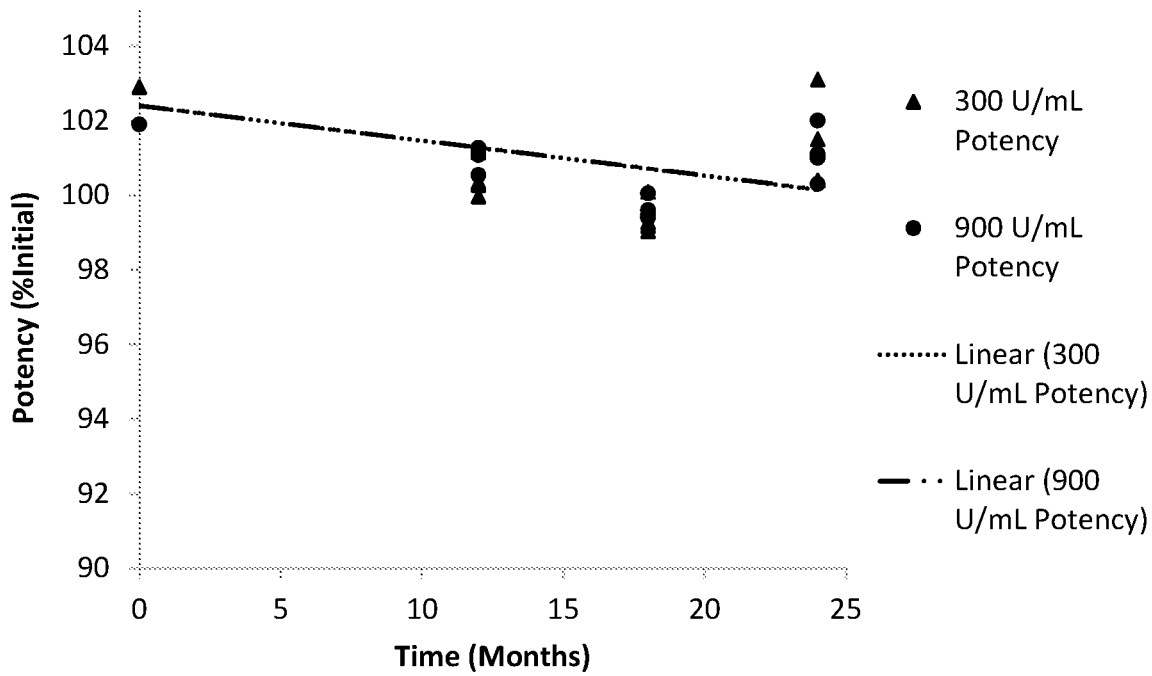
FIG. 5 shows the potency, as evidence by insulin concentration, of insulin formulations having 300 U/mL or 900 U/mL insulin, 0.39% zinc, 6 mM sodium, citrate, 70 mM sodium chloride, at pH 7.5 overtime during cold storage according to some aspects.
Figure 6:
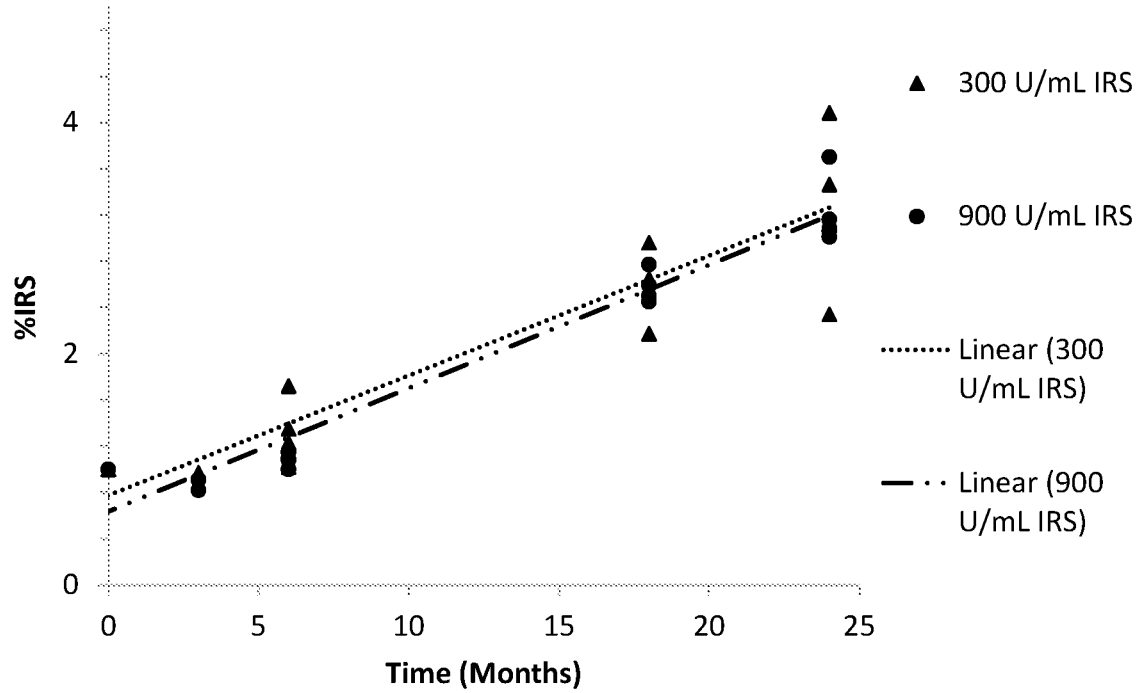
FIG. 6 shows the accumulation of IRS degradation products overtime at cold storage for the same formulation as in FIG. 5 according to some aspects.
Figure 7:
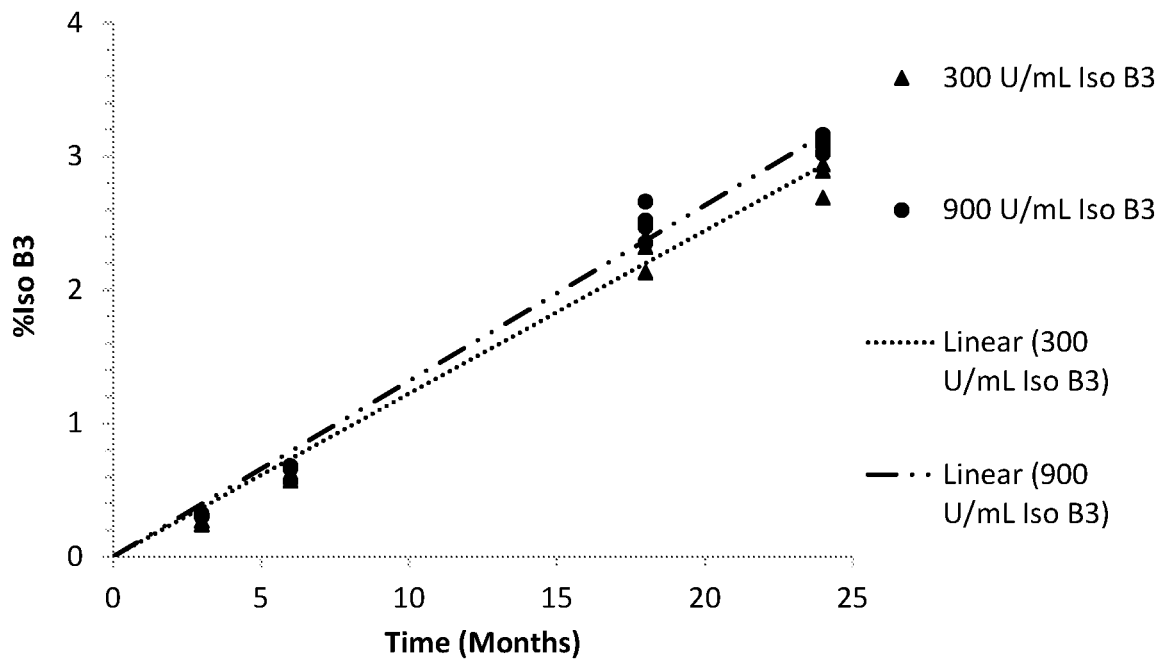
FIG. 7 shows the accumulation of Iso B3 degradation products overtime at cold storage for the same formulation as in FIG. 5 according to some aspects.
Figure 8:
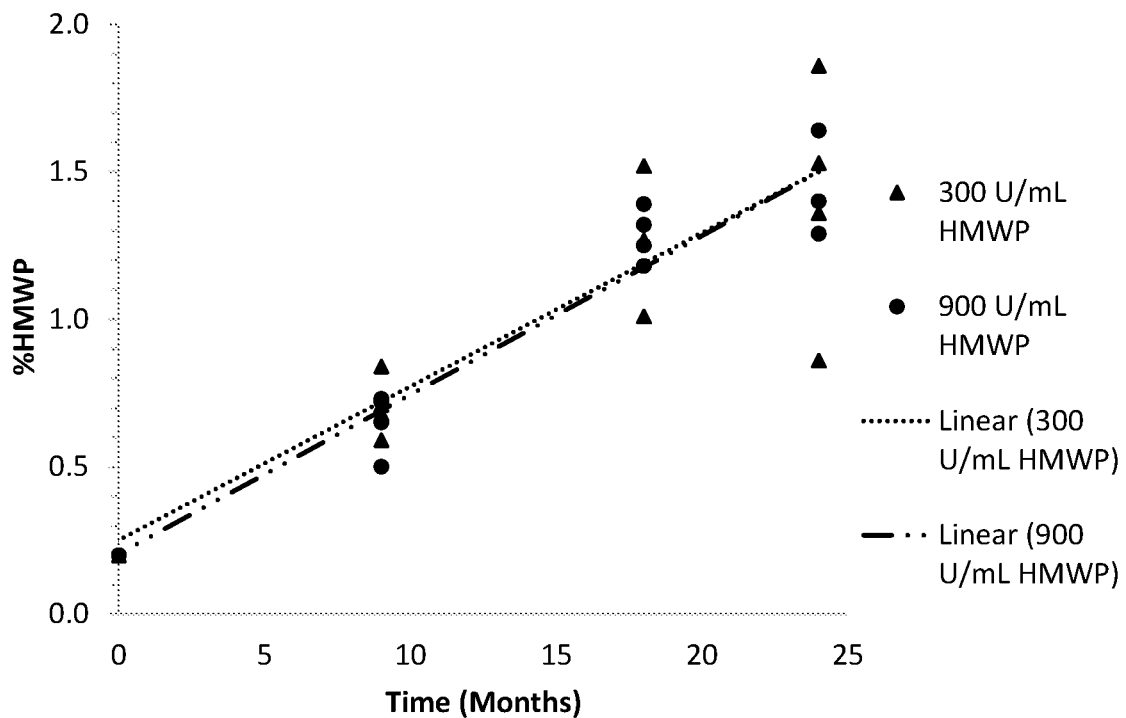
FIG. 8 shows the accumulation of high molecular weight polymers (HMWP) degradation products overtime at cold storage for the same formulation as in FIG. 5 according to some aspects.

In some instances, as described in Example 3, formulations having 300 U/mL and 900 U/mL generally have similar chemical and physical stability over time. For example, as shown in FIG. 5, the formulations may retain at least about 100-101% of the initial insulin after 12 months in storage at typical refrigeration temperatures (2-8° C., approx. 5° C.). In some instances, also as shown in FIG. 5, the formulations may retain at least about 98% of the initial concentration of insulin in solution after 18 months in storage at typical refrigeration temperatures (2-8° C., approx. 5° C.). In certain instances, also as shown in FIG. 5, the formulations may retain at least about 100% of the initial concentration of insulin in solution after 24 months in storage at typical refrigeration temperatures (2-8° C., approx. 5° C.). In some instances, as described in Table 7 and Table 8, the formulations may show a potency of about 99% after 18 months of storage at typical refrigeration conditions. In some instances, as described in Table 7 and Table 8, the formulations may show a potency of about 101% after 24 months of storage at typical refrigeration conditions. For example, the formulations may not exhibit a significant drop in potency over time. In some instances, such as shown in FIG. 6, the formulations may accumulate only about 1-2% IRS after 6 month at typical refrigeration temperatures. Also, in some instances, such as shown in FIG. 6, the formulations may accumulate only about 2-3% IRS after 18 month at typical refrigeration temperatures. Also, in some instances, such as shown in FIG. 6, the formulations may accumulate only about 2-4% IRS after 24 month at typical refrigeration temperatures. For example, the formulations may show % IRS accumulation of about 2.5-2.7% after 18 months of storage at typical refrigeration conditions, as described in Table 7 and Table 8. In some instances, the formulations may show % IRS accumulation of about 2.9-3.1% after 24 months of storage at typical refrigeration conditions, as described in Table 7 and Table 8. In certain instances, as shown in FIG. 7, the formulations may accumulate only about 0.5-0.7% Iso B3 after 6 month at typical refrigeration temperatures. In some instances, as shown in FIG. 7, the formulations may accumulate only about 2.0-2.8% Iso B3 after 18 month at typical refrigeration temperatures. In certain instances, as shown in FIG. 7, the formulations may accumulate only about 2.6-3.3% Iso B3 after 24 month at typical refrigeration temperatures. For example, the formulations may show % Iso B3 accumulation of about 2.29-2.45% after 18 months of storage at typical refrigeration conditions, as described in Table 7 and Table 8. In some instances, the formulations may show % Iso B3 accumulation of about 3.26-3.23% after 24 months of storage at typical refrigeration conditions, as described in Table 7 and Table 8. In some instances, as shown in FIG. 8, the formulations may accumulate only about 0.4-0.9% HMWP products after 9 month at typical refrigeration temperatures. In some cases, as shown in FIG. 8, the formulations may accumulate only about 1.0-1.6% HMWP after 18 month at typical refrigeration temperatures. In some instances, as shown in FIG. 8, the formulations may accumulate only about 0.8-1.9% HMWP after 24 month at typical refrigeration temperatures. For example, the formulations may show % HMWP product accumulation of about 1.29-1.33% after 18 months of storage at typical refrigeration conditions, as described in Table 7 and 8. In some instances, the formulations may show % HMWP product accumulation of about 1.40-1.43% after 24 months of storage at typical refrigeration conditions, as described in Table 7 and 8. As described in Example 3, pH of the formulations may stay stable over 24 months at typical refrigeration temperatures. In some instances, the formulations may contain 31.23 mg/mL (900 U/mL) or 10.41 mg/mL (300 U/mL) insulin, 6 mM citrate, and 70 mM NaCl, with 0.39% w/w zinc to insulin (2.0 zinc per insulin hexamer) at pH 7.5, as described in Table 7 and Table 8 and FIGS. 5-8.

In certain instances, as described in Example 4, the stability of insulin in the formulations may be impacted by pH and zinc concentration. For example, as shown in FIGS. 9-12, the solubility of insulin may be greater (improved) in formulations having higher pH (such as at least pH 7.2) and lower zinc concentration (such as less than or equal to about 0.5% wt/wt zinc to insulin, 2.7 zinc per insulin hexamer). In one example, as shown in Example 4 and FIG. 12, the solubility of insulin decreases below pH 7.2, particularly when the zinc concentration increases. In some instances, the formulations may contain 35 mg/mL (1009 U/mL) insulin, 6 mM citrate, and 70 mM NaCl as described in FIGS. 9-12. In some instances, the formulations are stable for at least 25 weeks under such conditions.

Figure 14:
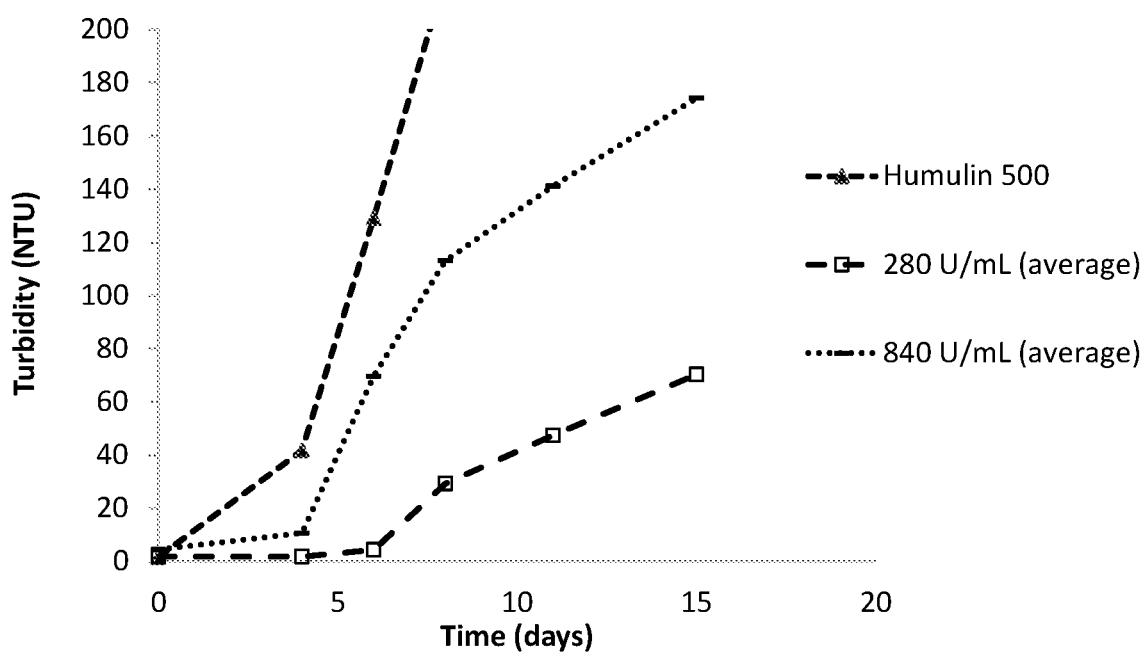
FIG. 14 shows a stability assessment following exposure to shear forces of preservative free formulations containing 280 U/mL and 840 U/mL insulin in comparison to commercial Humulin R® U-500 as in FIG. 13, according to some aspects. Formulations were shaken over a period of 15 days, and then turbidity was assessed using a nephelometer. Turbidity is shown plotted against time. The turbidity reading for the Humulin formulation reached the maximum threshold for the device by day 8.
Figure 15:
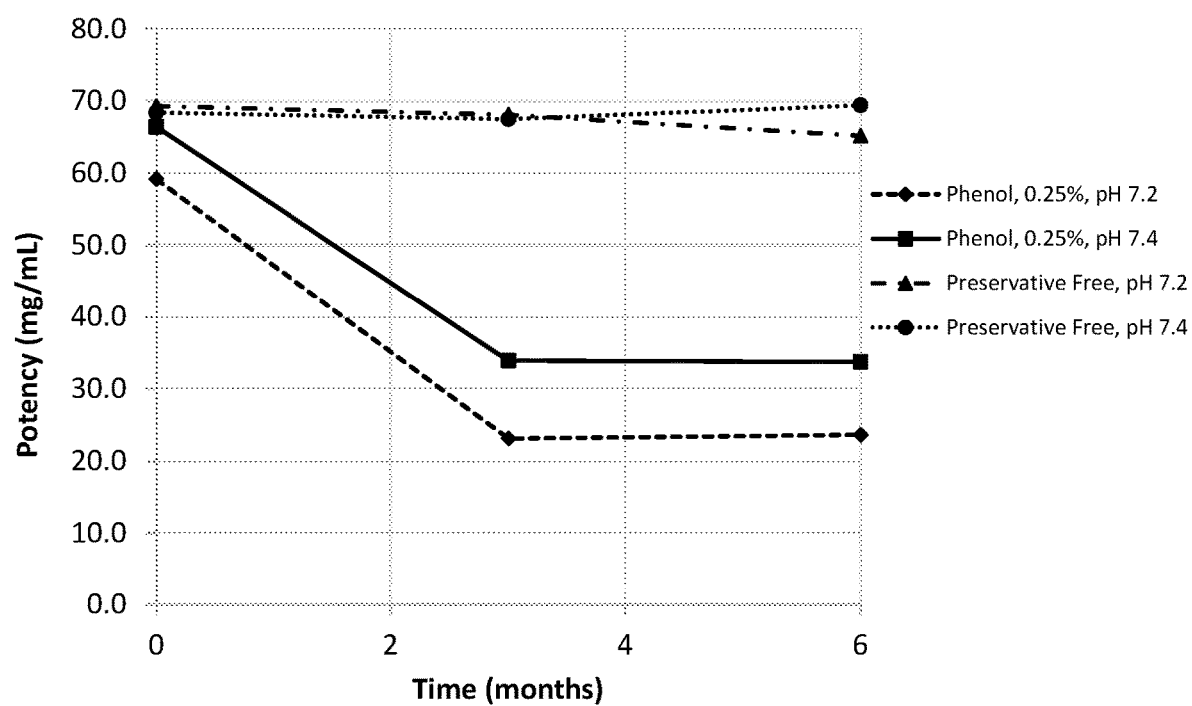
FIG. 15 shows the impact of adding phenol on the chemical stability of high concentration insulin formulations over time in cold storage according to some aspects. Formulations containing 70 mg/ml insulin at pH 7.2 and 7.4, including batches containing 0.25% v/v phenol ("phenol") and not containing phenol ("preservative free"), were prepared. The formulations were assessed at time 0, 3 months, and 6 months. Insulin concentration (potency) was measured by HPLC and potency plotted against time.

In some instances, as described in Example 5, the disclosed insulin formulations may be physically stable when exposed to shear forces. Formulations experience shear forces during shipment, handling, and typical use of the product by a subject. A factor that influences shear force includes the movement of formulation within the container. As such, experiments in which a formulation is shaken under controlled conditions are often used as a laboratory model for assessing the impact of shear forces on a formulation. As discussed above, insulin formulations may reflect instability by the formation of insulin fibrils, which may aggregate and come out of solution. Fibril formation decreases the potency of a formulation and can promote further destabilization via additional fibrillation. In addition, the fibril sediment is undesirable for therapeutic formulations, particularly inhaled formulations delivered into the respiratory system. In some instances, as shown in Table 10 and FIG. 13, the provided insulin formulations may retain greater than 90% potency (original insulin concentration) when exposed to constant agitation shear forces over a period of 26 days (refrigerated conditions). In some cases, the formulations are substantially more stable than commercial Humulin R® U-500 formulation (containing 0.25% wt/wt phenol) that retains less than 50% potency over the same period of time. In some instances, turbidity of a formulation may be used to assess insulin aggregation. For example, as shown in Table 11 and FIG. 14, the agitated formulations described in Example 5 and discussed with respect to FIG. 13, may have increased turibity after 5 days of constant agitation. In some instances, increased insulin concentration may facilitate fibrilation in a formulation, as shown by the increased rate of at which the 840 U/mL formulation becomes increasing turbid as compared to the 280 U/mL formulation. In some instances, the preservative free formulations of the disclosure show substantially less fibrillation as detected by turbidity as compared to the commercial Humulin R® U-500 formulation over a period of 8 days, as shown in FIG. 14. In some instances, the preservative free formulations of the disclosure may experience a cumulative loss of potency of about 0.5-1.7 mg/mL over a period of 28 days when exposed to shear forces. This is in contrast to an 8.9 mg/mL loss of potency observed under the same conditions for the commercial Humulin R® U-500 formulation. In some instances, the disclosed formulations may experience about 4-18 fold less loss in potency as compared to the commercial Humulin R® U-500 formulation. Said another way, the commercial Humulin R® U-500 formulation may experience about 4-18 fold greater loss in potency as compared to the disclosed formulations. In some instances, the formulations may contain containing 280 U/mL (29.2 mg/mL) and 840 U/mL (9.7 mg/mL) insulin, 6 mM citrate, 70 mM NaCl, 2.6 zinc molecules per hexamer, at pH 7.55 as described in FIGS. 9-12.

In some instances, the disclosed preservative-free formulations may be more stable than similar formulations containing phenol as a preservative/stabilizer as described in Example 6. For example, as shown in Table 12 and FIG. 15, insulin formulations containing saturating amounts of insulin at either pH 7.2 or pH 7.4 may retain at least 90% potency (original insulin concentration) over 6 months in refrigerated storage. In another example, similar formulations that also included 0.25% wt/vol phenol retained only between 20% and 35% potency over 6 months. In some instances, approximately 6% more insulin may be retained in the preservative free formulations at pH 7.4 as compared to pH 7.2 after 6 months in storage. In other instances, approximately 15% more insulin may be retained in the phenol containing formulations at pH 7.4 as compared to pH 7.2 after 6 months in storage. In some instances, the phenol containing formulations may become instable quickly, losing potency within a day, as shown in Table 12 and FIG. 15, with a greater loss at pH 7.2 than at pH 7.4. In some instances, the provided formulations may contain containing 2017 U/mL (70 mg/mL) in 6 mM citrate and 70 mM NaCl, with 2.6 zinc molecules per insulin hexamer at pH 7.2 or 7.4 as described in Table 12 and FIG. 15.

A further aspect is that the formulation may be packaged as a single use "unit dose" container or as a multi-dose container. In some instances, a unit dose of the insulin formulations described in this disclosure is provided.

Examples of single use containers are blister packs or capsules. Examples of multi-dose containers are drop dispensers, or vials.

In some instances, provided is an insulin formulation that includes insulin at a minimum concentration of 1-13 mM, a salt at a concentration of 50-150 mM, a pH buffering agent at a concentration of 3-24 mM, zinc at a ratio of 1.9-2.7 zinc ions per insulin hexamer, and a pH in the range of 7.2 to 8.0, but does not contain preservatives or stabilizers. In some instances, the formulations may have an insulin concentration of 6-76 mg/mL. In some instances, the formulations may have an insulin concentration of 173 U/mL to 2189 U/mL. In some instances, the insulin may be human insulin. In some cases, the formulation may include at least 30 mg/mL insulin or at least 5.17 mM insulin or at least 864 U/mL insulin. In some instances, the formulation may contain 10-30 mg/mL insulin or 1.72-5.17 mM. In some instances, the insulin formulation may have an insulin concentration of about 30 mg/mL or 5.17 mM or 864 U/mL and a pH of about 7.55. In some cases, the insulin concentration may be 30 mg/mL or 5.17 mM or 864 U/mL and the pH may be 7.55. In some instances, the pH of the formulation may be in the range of 7.4 to 7.6. In some instances, the salt may be a chloride salt. In some cases, the salt may be sodium chloride (NaCl). In some instances, the pH buffering agent may be citrate. In one example, the pH buffering agent may be sodium citrate. In some instances, the tonicity (ionic strength) of the formulation may be 100-300 mOsm. In some cases, the formulation may contain 70 mM NaCl or a salt having similar ionic strength. In some instances, the formulation does not contain surfactants. In some cases, the formulation may be administrable by inhalation or injection. In some instances, the formulation may be administrable by an inhalation device. In some instances, the formulation may be aerosolizable. In some instances, provided is a unit dose of an insulin formulation as described in this paragraph or elsewhere in this disclosure.

IV. Kits

Another aspect of this disclosure is kits containing the insulin formulations described in Section III and elsewhere in this disclosure. In some instances, the kits may include one or more unit doses of a described insulin formulation and a device for administering the formulation. Kits may include a single use "unit dose" container or a multi-dose container. Examples of single use containers are blister packs or capsules. Examples of multi-dose containers are drop dispensers, or vials. In some instances, the device for administering the formulation may be an aerosolization device. For example, in some instances, the device may be an aerosolizer, an inhaler, or a nebulizer. Exemplary aerosolization devices that may be included in the kit are described in U.S. Patent Application Publication Nos. 20110168172; 20110017431; 20130269684; 20130269694; and 20130269684; U.S. application Ser. Nos. 14/743,763; 14/743,711; 14/732,247; and 14/732,446; and International PCT Publication Nos. WO 2013/158352 and WO 2013/158353, each of which is incorporated herein by reference in their entirety. Other devices for aerosolization of liquid formulations are well-known in the art. In some instances, the kits may include a device for administrating the formulation via injection. For example, the kits may include one or more syringes. In another example, the kits may include one or more needles. In another example, the kits may include one or more syringes and one or more needles. The kits may also include a pump or a pen device for administering the formulation via injection. In some instances, the kit may include instructions describing use of the device to administer the formulation.

V. Methods of Treatment

As noted above, certain embodiments and aspects of the present disclosure relate to a method of treating a subject having diabetes mellitus using the formulations described in Section III and elsewhere in this disclosure. In one aspect, the method can include administering to a subject having diabetes mellitus a therapeutically effective amount of the formulation. The formulation can be administered to the subject via inhalation or injection. For example, the formulation can be administered using an inhalation device such as an aerosolizer, an inhaler, or a nebulizer, or by injection (intravenous, intramuscular, intraperitoneal), including by pump or pen.

Exemplary aerosolization devices for administering the provided preservative free formulations are described in U.S. Patent Application Publication Nos. 20110168172; 20110017431; 20130269684; 20130269694; and 20130269684; U.S. application Ser. Nos. 14/743,763; 14/743,711; 14/732,247; and 14/732,446; and International PCT Publication Nos. WO 2013/158352 and WO 2013/158353, each of which is incorporated herein by reference in their entirety. Other devices for aerosolization of liquid formulations such as those described herein are well-known in the art.

In one aspect, a therapeutically effective amount of the formulations may be 20 U to 500 U delivered via the pulmonary route, with a typical dosage being 150 U. In some instances, a therapeutically effective amount of the formulations delivered via the pulmonary route may be 150 U. In one aspect, a therapeutically effective amount of the formulations may be 2 U to 28 U delivered via subcutaneous injection, with a typical dosage being 21 U. In some instances, a therapeutically effective amount of the formulations delivered via subcutaneous injection may be 21 U. Typical dosing varies with route of administration because pulmonary efficiency is approximately 5%-30% of the efficiency of the subcutaneous route. For reference, 1 U is equivalent to 0.0347 mg of human insulin (28.8 U/mg).

In some cases, suitable dosing with an insulin formulation by pulmonary delivery, such as through inhalation of an aerosolized formulation, is performed using formulations with at least 6 mg/mL (1 mM; 168 U/mL) to achieve the desired dosage with minimal administrations. For example, if the insulin formulation has a low concentration, repeated administrations may be required to achieve the desired dosage. In one aspect, the efficiency of delivery of insulin into the blood via the inhalation pathway is approximately 8-20% relative to the injectable route. In one aspect, the relative efficiency is 14%. In some aspects, the insulin formulation can administer a dose of 200 U/mL insulin to a subject via inhalation of the aerosolized formulation in one or two administrations, in particular, via one or two inhalations by a subject. In some instances, the insulin concentration of the formulation may be in the range of 1-13 mM (or 6-76 mg/mL or 173-2189 U/mL) to provide a sufficient dosage with minimal administrations. In some instances, the insulin concentration of the formulation may contain 10-30 mg/ml insulin (1.72-5.17 mM) to provide a sufficient dosage with minimal administrations. In some instances, the insulin concentration of the formulation may contain at least 30 mg/ml insulin to provide a sufficient dosage with minimal administrations.

In another aspect, the formulation is administered prior to the subject eating a meal. For example, the formulation may be administered just prior to the subject eating a meal. In another example, the formulation may be administered at least 15 minutes prior to the subject eating a meal. In some examples, the formulation may be administered at least once a day. In certain instances, the formulation may be administered up to 1, 2, 3, or 4 times per day.

VI. Examples

The following examples are offered to illustrate, but not to limit, the claimed invention.

Example 1

Purpose: To establish the chemical stability of buffered insulin formulations containing 900 U/mL (31.2 mg/mL, 5.37 mM) insulin in 70 mM sodium chloride, with a variety of pH buffering agents to identify a pH buffering agent to maintain stable insulin in formulation. This study looks specifically at the buffer type as a variable. The insulin and sodium chloride levels were held constant. Insulin concentration was fixed at 900 U/mL (31.2 mg/mL).

Formulation Components: The formulations were made using USP recombinant human insulin (Sanofi-Aventis, Material: 192228, GMID: 341921), which contained 0.42% w/w zinc to insulin (about 2.2 zinc per six insulin monomers). The following materials were obtained from JT Baker: USP sodium citrate dihydrate; USP Trizma® Base; USP sodium phosphate, monobasic; HPLC grade water; hydrochloric acid (37%), zinc chloride, and sodium hydroxide pellets.

Method Description: Six separate formulations were prepared. For each, recombinant human insulin was weighed and dissolved to 80% of final volume in 87.5 mM hydrochloric acid. Buffer (citrate, Tris, phosphate, or no buffer) was weighed into each formulation to concentrations listed in Table 1, relative to final dilution volume. For the +1 Zn condition, zinc chloride was added to a final zinc concentration of 0.61% w/w zinc to insulin. Sodium hydroxide (1M) was added to adjust the pH to 7.5. The formulation was adjusted to final volume with water and the pH was rechecked, and, if necessary, re-adjusted to pH 7.5.

TABLE 1

Buffers/Concentrations

| Buffer | Concentration | pH |
|---|---|---|
| Citrate | 15 mM | 7.5 |
| Citrate/Tris | 15 mM/20 mM | |
| Tris | 20 mM | |
| Tris + 1 Zn | 20 mM | |
| Phosphate | 5 mM | |
| Reference (no buffer) | — | |

Procedure: Each formulation was placed into refrigerated storage (2-8° C.; approx. 5° C.). Refrigerated formulations were stored for up to 23 months and were sampled at two or more of time points 0, 6, 12, 18 and 23 months. Samples were analyzed by High Performance Liquid Chromatography at time points from 0 to 23 months. Each sample was analyzed by Reverse Phase High Performance Liquid Chromatography (RP-HPLC) for insulin related substances (IRS) and Iso B3 at 5° C. at the start of the experiment and then at 6 months, 12 months, 18, months, and 23 months.

HPLC Assays: The content of Iso B3 and Insulin Related Substances (IRS) was measured by an Reversed Phase (RP)-HPLC method using a C-18, 3×250 mm column on a Waters (Milford, Mass.) HPLC module with diode array detector. The detector was set at 214 nm. Flow rate was 0.55 mL/minute. Samples were diluted in 100 mM phosphate buffer, pH 7.8 and tested at 2 mg/ml concentration. For Iso B3 assessment, mobile phase A was 7% acetonitrile and 93% 140 mM sodium perchlorate (pH adjusted to 2.3 with phosphoric acid) and mobile phase B was 57% acetonitrile, 65 mM sodium perchlorate (pH adjusted to 2.3 with phosphoric acid). The assay conditions were isocratic at 55% B for the first 30 minutes, from 30 to 56 minutes there was a gradient to 80% B, and after 56 minutes, the mobile phase percentages were returned to initial conditions. For IRS assessment, the mobile phase A was 18% acetonitrile, 82% 200 mM sodium sulfate (pH adjusted to 2.8 with phosphoric acid) and mobile phase B was 50% acetonitrile, 50% 200 mM sodium sulfate (pH was adjusted to 2.8 with phosphoric acid). The initial starting condition were isocratic at 22-30% B for 32 minutes, the % B was adjusted for insulin retention time between 17-24 minutes, from 32-57 minutes the % B was increased in a linear gradient to 52% B, and at 57 minutes mobile phases return to starting conditions.

The HPLC chromatograms were evaluated to determine the area of insulin degradation product peaks relative to intact insulin. The total percent of degradation products are referred to as Insulin Related Substances (% IRS). These included all insulin related degradation peaks except the A21 and Iso B3 desamido peaks. These two substances are addressed separately by the USP and EP Monographs and are not typically included in % IRS. The area represented by the IRS peaks as a percent of total insulin (all peaks) was determined, and the data points were analyzed by linear regression to establish trend lines. % Iso B3 and % IRS change per month were calculated from the slope of trend lines.

Results: The analytical results for this experiment are shown in Table 2 and Table 3 and graphically in FIG. 1 and FIG. 2 and are described below. The 20 mM Tris+1 Zn (0.61% wt/wt zinc to insulin) physically precipitated, resulting in a small potency drop (data not shown). The Reference (no buffer) solution is identified in FIGS. 1-2 as "NaCl".

TABLE 2

Chemical Stability of Insulin vs. Buffer Type - Area % Iso B3 (5° C.)

| Buffer | 0 mo | 6 mo | 18 mo | 23 mo | % Iso B3/mo |
|---|---|---|---|---|---|
| Reference (no buffer) | 0.05 | 0.97 | NS | 4.74 | 0.21 |
| NaCl/Phosphate | 0.05 | 1.32 | NS | 5.75 | 0.25 |
| 20 mM Tris | 0.05 | NS | 4.09 | NS | 0.23 |
| 20 mM Tris + 1 Zn | 0.05 | NS | 4.46 | NS | 0.25 |
| 15 mM Citrate | 0.05 | NS | 2.46 | NS | 0.14 |
| 15 mM Citrate/10 mM Tris | 0.05 | NS | 2.54 | NS | 0.14 |

NS = Not Sampled

TABLE 3

Chemical Stability of Insulin vs. Buffer Type - Area % IRS (5° C.)

| Buffer | 0 mo | 6 mo | 12 mo | 18 mo | 23 mo | % IRS/mo |
|---|---|---|---|---|---|---|
| Reference (no buffer) | 0.52 | 1.02 | NS | 1.83 | 2.45 | 0.11 |
| NaCl/Phosphate | 0.52 | 1.01 | NS | 2.23 | 2.76 | 0.12 |
| 20 mM Tris | 0.52 | NS | 1.72 | 1.78 | NS | 0.10 |

TABLE 3-continued

Chemical Stability of Insulin vs. Buffer Type - Area % IRS (5° C.)

| Buffer | 0 mo | 6 mo | 12 mo | 18 mo | 23 mo | % IRS/mo |
|---|---|---|---|---|---|---|
| 20 mM Tris + 1 Zn | 0.52 | NS | 1.62 | 1.64 | NS | 0.09 |
| 15 mM Citrate | 0.52 | NS | 2.00 | 1.86 | NS | 0.10 |
| 15 mM Citrate/ 10 mM Tris | 0.52 | NS | 2.41 | 2.60 | NS | 0.14 |

NS = Not Sampled

Iso B3 forms more quickly as pH increases (see Example 1). Buffer solutions limit pH changes by absorbing environmental protons and electrons. The results in Table 2 show that the rate of formation of Iso B3 at 5° C. ranges from 0.14-0.25% per month depending on the selected buffer type. This data suggests reduced rates of Iso B3 formation when the buffer used to control pH includes citrate. Tris, phosphate, and unbuffered solutions show significantly higher rates of Iso B3 formation relative to citrate-containing formulas, despite each solution maintaining a pH of 7.5.

Formation of IRS range from 0.11-0.12% per month, with the exception of the citrate/Tris combination, which formed IRS at 0.14% per month. These results suggest that the formation of insulin dimers and hydrolysis products other than Iso B3 are generally similar regardless of buffer. The combination of Tris and citrate shows slightly higher % IRS, which may be the result of a number of factors including the presence of two buffer types or the increased osmolality of the solution.

This study suggests that citrate buffer buffers pH sufficiently to both limit insulin hydrolysis (Iso B3) and covalent dimer formation (IRS).

Example 2

Purpose: To establish the chemical stability of buffered insulin formulations containing 900 U/mL (31.2 mg/mL, 5.37 mM) insulin in 6 mM sodium citrate and 70 mM sodium chloride over a range of pH values to identify a pH range to maintain stable insulin in formulation. This study looks specifically at the pH as a variable. The insulin, sodium chloride, and sodium citrate levels were held constant.

Formulation Components: The formulations were made using USP recombinant human insulin (Sanofi-Aventis, Material: 192228, GMID: 341921), which contained 0.42% wt/wt zinc to insulin (about 2.2 zinc per six insulin monomers). The following materials were obtained from JT Baker: USP sodium citrate dihydrate; HPLC grade water; hydrochloric acid (37%), and sodium hydroxide pellets.

Method Description: Recombinant human insulin was weighed and dissolved to 80% of final volume in 87.5 mM hydrochloric acid. Sodium citrate dihydrate was added to the formulation to a concentration of 6 mM (relative to the final dilution volume). Sodium hydroxide (1M) was added to adjust the pH to 7.0. The formulation was adjusted to final volume with water and the pH was rechecked. This bulk formulation was aliquoted into 6 separate glass containers with Teflon™ seals and screw-cap closures. The pH of each separate container was carefully adjusted to a different pH value: 7.0, 7.2, 7.4, 7.6, 7.8, and 8.7 with small volumes of sodium hydroxide.

Procedure: An aliquot of each formulation was placed into refrigerated storage (2-8° C., approx. 5° C.). An aliquot of each formulation was also stored at 25° C. (incubator). Refrigerated formulations were stored for up to 24 months and were sampled at time 0, 5, 9, 15, 18, and 24 months. Samples stored at 25° C. were held for 2 weeks and then sampled. Samples were analyzed by HPLC to determine % Iso B3 content and % IRS content as described in Example 1.

Figure 3:
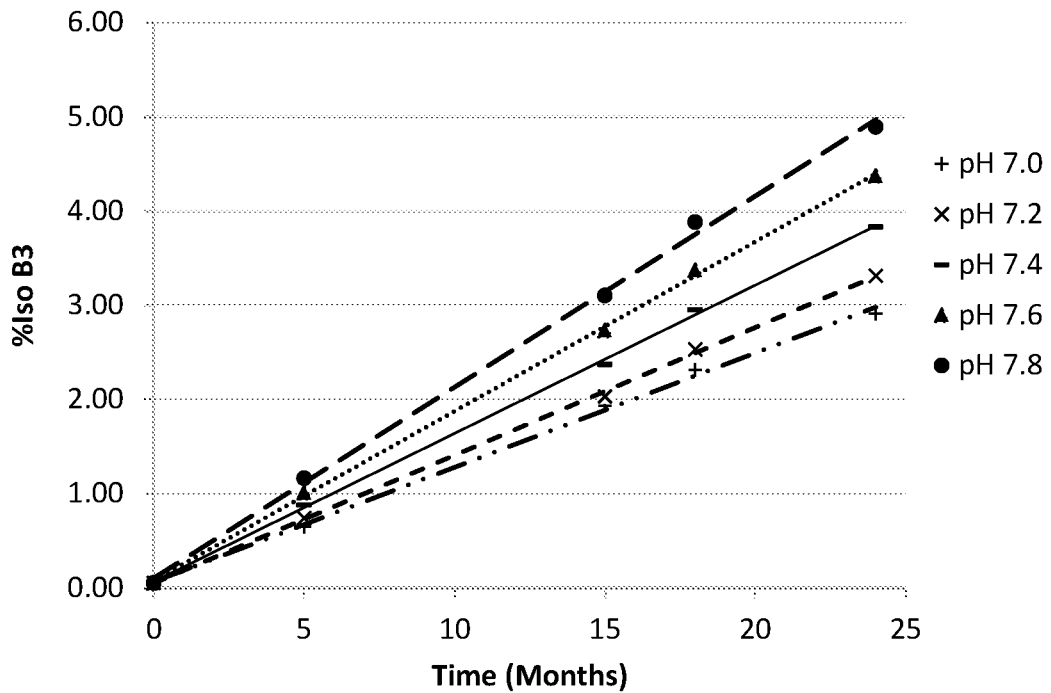
FIG. 3 shows the chemical stability, as evidenced by Iso B3 insulin degradation product formation overtime, of insulin formulations having different pH values according to some aspects.
Figure 4:
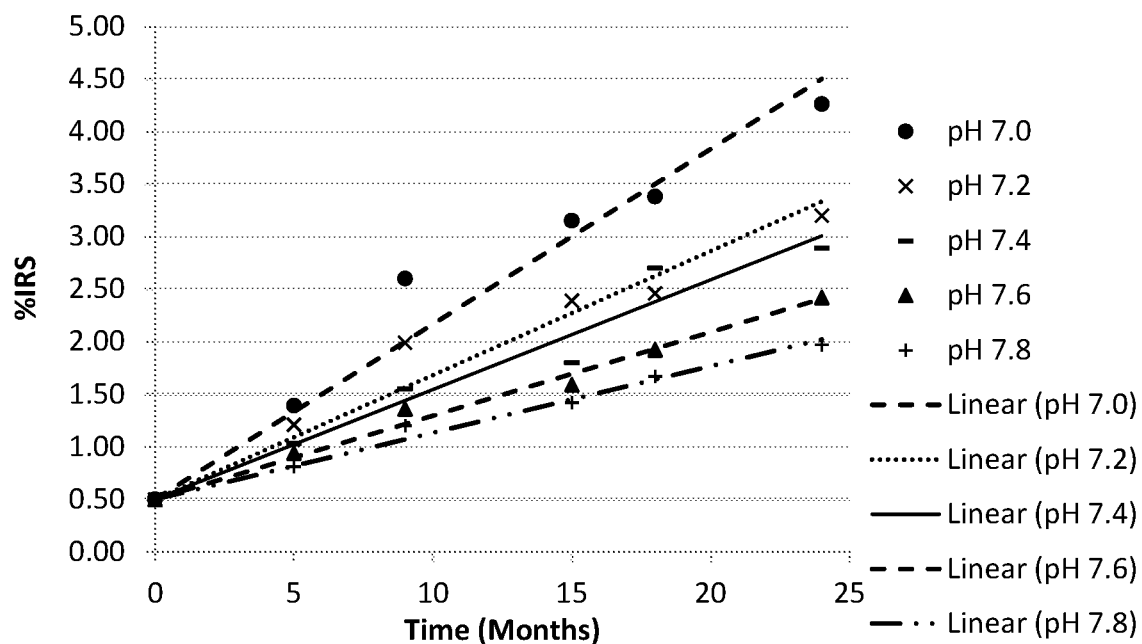
FIG. 4 shows the chemical stability, as evidenced by IRS degradation product formation overtime, of the same insulin formulations as shown in FIG. 3 according to some aspects.

Results: The analytical results for this experiment are shown in Tables 4-6 and are described below. FIG. 3 and FIG. 4 show the growth rate of Iso B3 and IRS, respectively, across 15-18 months at 5° C. for each pH condition. The data points were analyzed by linear regression to establish trend lines. % Iso B3 and % IRS change per month were calculated from the slope of trend lines.

TABLE 4

Chemical Stability of Insulin by pH - Area % Iso B3 (5° C.)

| | Time (mo): | | | | | |
|---|---|---|---|---|---|---|
| | 0 | 5 | 15 | 18 | 24 | % Iso B3/mo |
| pH 7.0 | 0.05 | 0.65 | 1.93 | 2.31 | 2.91 | 0.12 |
| pH 7.2 | 0.05 | 0.74 | 2.03 | 2.53 | 3.31 | 0.14 |
| pH 7.4 | 0.05 | 0.88 | 2.37 | 2.95 | 3.83 | 0.16 |
| pH 7.6 | 0.05 | 1.01 | 2.73 | 3.37 | 4.37 | 0.18 |
| pH 7.8 | 0.05 | 1.16 | 3.10 | 3.88 | 4.89 | 0.20 |

TABLE 5

Chemical Stability of Insulin vs. pH - Area % IRS (5° C.)

| | Time (mo): | | | | | |
|---|---|---|---|---|---|---|
| | 0 | 5 | 9 | 15 | 18 | 24 | % IRS/mo |
| pH 7.0 | 0.50 | 1.39 | 2.60 | 3.15 | 3.38 | 4.26 | 0.15 |
| pH 7.2 | 0.50 | 1.21 | 1.99 | 2.39 | 2.46 | 3.20 | 0.11 |
| pH 7.4 | 0.50 | 1.03 | 1.55 | 1.80 | 2.70 | 2.89 | 0.10 |
| pH 7.6 | 0.50 | 0.94 | 1.36 | 1.59 | 1.92 | 2.42 | 0.08 |
| pH 7.8 | 0.50 | 0.81 | 1.20 | 1.42 | 1.67 | 1.97 | 0.06 |

The relationship between pH and insulin degradation is complex. In order to maximize the stability of an insulin formulation it is very important to control pH. The results in Table 5 show that the rate of formation of IRS at 5° C. decreases with increasing pH from 0.15% per month at pH 7.0 to 0.06% per month at pH 7.8. The increase of pH has the opposite effect on the generation of Iso B3, as shown in Table 4, where the rate of formation increases with increasing pH from 0.12% per month at pH 7.0 to 0.20% per month at pH 7.8. As pH increases, Iso B3 formation increases and IRS formation declines (pH range: 7.4-8.0). At pH greater than 8.0, hydrolysis of insulin appears to occur at a more rapid rate.

The increased levels of Iso B3 observed are less significant to the stability of the formulation than the decreased levels of IRS, even at the highest pH because Iso B3 remains largely bioactive (it retains >90% of the insulin activity). As such, insulin formulations at pH 7.6 and pH 7.8 retain potency, and this level of Iso B3 formation is acceptable for commercial formulations.

Table 6 shows the formation of Iso B3 at 25° C. storage for 2 weeks. Iso B3 formation occurred rapidly with increased temperature (25° C.) and pH (pH 8.7).

TABLE 6

Chemical Stability of Insulin by pH - Area % Iso B3 (25° C.)

| 2 Week Time Point | Iso B3 (% Area) |
|---|---|
| pH 7.4 | 1.08 |
| pH 7.6 | 1.19 |
| pH 7.8 | 1.33 |
| pH 8.7 | 1.96 |

This study suggests that maintaining the pH range of the formulation between 7.4 and 7.8 limits insulin hydrolysis (Iso B3) and covalent dimer formation (insulin related substances) sufficiently in long term storage conditions.

Example 3

Purpose: This study assessed formulations having different insulin concentrations in glass containers outfitted with drop dispensers simulating commercial packaging in order to determine the anticipated shelf life (stability) of the insulin formulations. The chemical stability of buffered insulin formulations containing 10.41 mg/mL (300 U/mL, 1.79 mM) and 31.23 mg/mL (900 U/mL, 5.38 mM) insulin (0.39% zinc w/w zinc to insulin) at pH 7.5 in 6 mM sodium citrate and 70 mM sodium chloride was assessed over 24 months.

Formulation Components: The formulations were made using USP recombinant human insulin (Sanofi-Aventis, Material: 192228, GMID: 341921), which contained 0.39% w/w zinc to insulin (about 2.2 zinc per six insulin monomers). The following materials were obtained from JT Baker: USP sodium citrate dehydrate, HPLC grade water, hydrochloric acid (37%), and sodium hydroxide pellets.

Method Description: Recombinant human insulin was dissolved to 80% of final volume in 87.5 mM hydrochloric acid. Sodium citrate was weighed into the formulation at 6 mM concentration (relative to the final dilution volume). Sodium hydroxide (1 M) was added at 7% of final volume. Formulations were brought to final volume with water. The pH was checked, and adjusted to final pH of 7.5 with sodium hydroxide. Final batch volumes of 1 L; final insulin concentrations: 10.41 mg/mL (300 U/mL, 1.79 mM) and 31.23 mg/mL (900 U/mL, 5.38 mM).

Procedure: Each formulation was aliquoted into 4 glass containers and outfitted with drop dispensers. The fill volume was 8 mL. Vials were purchased from Gerresheimer, 10 mL volume, part #F008X1P20-0150. Drop dispensers were purchased from Aero Pump, PN #70019500. These drop dispensers represented an example of final packaging. Samples were assessed at time points from 0 to 24 months.

Potency was determined by RP-HPLC in comparison to a USP Human Insulin reference standard by following the USP monograph method. Iso B3 desamido and A21 content were determined by RP-HPLC as described in Example 1. The amount of high molecular weight polymers (HMWP) was determined by Size Exclusion-High Performance Liquid Chromatography (SEC-HPLC). Solubility was determined by visual inspection (observation of any crystal formation) and by potency measurement. pH was measured using a typical pH meter equipped with probe (Orion Star A211 with a Ag/AgCl combination pH semi micro epoxy electrode).

Stability parameters were measured against acceptance criteria that were set to establish a minimally stable formulation. Acceptance criteria were set based on US Pharmacopeia and European Pharmacopeia recommendations for insulin formulations and based on known criteria for the overall physical and chemical stability of insulin. The pH acceptance criteria was set based on the reduced solubility of insulin below pH 7.2 observed in Example 2 and increased hydrolytic reactions above pH 7.8. The acceptance criteria were set as follows: 90-110% potency, ≤6.0% IRS, ≤5.0% Iso B3, ≤5.0% A21, ≤2.0% HMWP, and pH at 7.2-7.8. Formulations meeting these acceptance criteria over a 24 month period will be considered sufficiently stable for commercialization.

The data points were analyzed by linear regression to establish trend lines for potency, % Iso B3, % IRS, and % HMWP. The trend lines were used to estimate the rate of change of purity and potency over the shelf life of the product and for prediction of the anticipated shelf life based on the set acceptance criteria.

Results: The analytical results for this experiment are shown in Tables 7 and 8 and FIGS. 5-8 and are described below. Data is n=4 replicates, presented as average±standard deviation.

TABLE 7

300 U/mL Insulin Formulation Stability Analysis

| | Acceptance Criteria | Time (months) | | | | | |
|---|---|---|---|---|---|---|---|
| | | 0 | 6 | 9 | 12 | 18 | 24 |
| Potency | 90-110% | 102.9 ± 0.7 | NS | NS | 100.4 ± 0.5 | 99.4 ± 0.5 | 101.5 ± 1.1 |
| % IRS | ≤6.0% | 0.52 ± 0.1 | 1.33 ± 0.3 | NS | NS | 2.69 ± 0.4 | 2.90 ± 0.7 |
| % Iso B3 | ≤5.0% | 0.03 ± 0.0 | 0.60 ± 0.0 | NS | NS | 2.29 ± 0.1 | 3.26 ± 0.2 |
| % A21 | ≤5.0% | 0.50 ± 0.0 | 0.48 ± 0.0 | NS | NS | 0.47 ± 0.0 | 0.47 ± 0.0 |
| % HMWP | ≤2.0% | 0.16 ± 0.0 | NS | 0.71 ± 0.1 | NS | 1.33 ± 0.2 | 1.40 ± 0.4 |
| pH | 7.2-7.8 | 7.39 ± 0.0 | 7.25 ± 0.0 | NS | 7.26 ± 0.0 | 7.27 ± 0.0 | 7.31 ± 0.0 |

NS: Not sampled.

TABLE 8

900 U/mL Insulin Formulation Stability Analysis

| | | Time (months) | | | | | |
|---|---|---|---|---|---|---|---|
| | Acceptance Criteria | 0 | 6 | 9 | 12 | 18 | 24 |
| Potency | 90-110% | 101.9 ± 0.7 | NS | NS | 101.0 ± 0.3 | 99.6 ± 0.3 | 101.1 ± 0.7 |
| % IRS | ≤6.0% | 0.52 ± 0.1 | 1.08 ± 0.1 | NS | NS | 2.58 ± 0.1 | 3.10 ± 0.3 |
| % Iso B3 | ≤5.0% | 0.03 ± 0.0 | 0.67 ± 0.0 | NS | NS | 2.45 ± 0.1 | 3.23 ± 0.1 |
| % A21 | ≤5.0% | 0.50 ± 0.0 | 0.46 ± 0.0 | NS | NS | 0.47 ± 0.0 | 0.47 ± 0.0 |
| % HMWP | ≤2.0% | 0.16 ± 0.0 | NS | 0.65 ± 0.1 | NS | 1.29 ± 0.1 | 1.43 ± 0.1 |
| pH | 7.2-7.8 | 7.40 ± 0.0 | 7.29 ± 0.0 | NS | 7.31 ± 0.0 | 7.29 ± 0.0 | 7.30 ± 0.0 |

NS: Not sampled.

The results in Tables 7 and 8 show a potency of 101.1-101.5% of target insulin concentration after 24 months of storage at 5° C. This result equates to a potency drop of 0.8-1.4%. The results are shown graphically in FIG. 5 (results are graphed as a percent of their initial value). The results are linear and indicate that potency remains within the established acceptance criteria of 90-110% of target for significantly longer than an anticipated 2 year product shelf life. Potency is predicted to reach 90% (minimum acceptance criteria) after 132 months based on the trend line slope.

The results in Tables 7 and 8 show insulin related substances (% IRS) of between 2.9%-3.1% after 24 months of storage at 5° C. This percentage is significantly lower than acceptance criteria of 6%. The results are shown graphically in FIG. 6. Based on the trend line, % IRS is predicted to reach the acceptance criteria of 6% after 50 months. This result indicates that IRS will be within acceptable limits during an anticipated 2 year product shelf life.

The results in Tables 7 and 8 show Iso B3 values of approximately 3.2% after 24 months of storage at 5° C. The results are shown graphically in FIG. 7. Trend data predicts that % Iso B3 will reach the acceptance criteria of 5% after 38 months. This result indicates that Iso B3 will be within acceptable limits during an anticipated 2 year product shelf life.

The results in Tables 7 and 8 show % HMWP values of approximately 1.4% after 24 months of storage at 5° C. The results are shown graphically in FIG. 8. Trend data predicts that % HMWP will reach the acceptance criteria of 2% after 33 months. This result indicates that % HMWP will be within acceptable limits during an anticipated 2 year product shelf life.

pH dropped slightly over the initial study period, followed by no significant trend. This result is consistent with typical aqueous solutions, which draw carbon dioxide from the environment, causing slight acidification. pH is predicted to be stable during an anticipated 2 year shelf life.

Student T-test analysis of the data indicated no significant difference (p>0.05) between the results observed for the 300 U/mL and 900 U/mL formulations. These results confirm the null hypothesis that the 300 U/mL and 900 U/mL formulations were acceptably similar.

Important criteria for determining shelf-life for an insulin formulation are potency (% of asserted/desired formulation concentration), IRS levels, and HMWP levels. Stability of pH is also important, particularly for very concentrated insulin formulations (for example, as saturation limit is neared) to avoid isoelectric precipitation or recrystallization of the insulin. The provided formulations remained very clear over the course of the study (indicating little, if any, protein precipitation) and within the set acceptance criteria. The formulations also showed remarkable stability at 5° C. for at least 2 years of refrigerated storage. The results of this study suggest that the described formulations provide acceptable long term stability at both 300 U/mL and 900 U/mL insulin by limiting the formation of Iso B3, IRS, and HMWP.

Example 4

Purpose: To assess the relationship between pH and zinc content on the physical stability of the insulin formulations and to identify the optimal ranges for these parameters to maintain physical stability of the insulin formulations. In this experiment, insulin, sodium chloride, and citrate ion were held constant. Zinc content and pH were varied.

Formulation Components: The formulations were made using USP recombinant human insulin (Sanofi-Aventis, Material: 192228, GMID: 341921), which contained 0.39% w/w zinc to insulin. The following materials were obtained from JT Baker: USP sodium citrate dihydrate; HPLC grade water; hydrochloric acid (37%), zinc chloride, and sodium hydroxide pellets.

Method Description: Four 35 mg/ml insulin (6.03 mM, 1008 U/mL) formulations were prepared. Formulations were prepared by adding sodium citrate dihydrate and sodium chloride to final concentrations of 6 mM and 70 mM, respectively. Sodium hydroxide was used to adjust the pH of the formulations to 7.0, 7.1, 7.2, and 7.3, respectively. These four formulations were each then separated into three equal parts. Additional zinc (in the form of zinc chloride) was spiked into one part at each pH in very small relative volumes (0.1-0.2% of final formulation volume). Final zinc concentrations were 0.39% w/w, 0.45% w/w, and 0.51% w/w zinc to insulin, equivalent to 2.08, 2.40, and 2.73 zinc per hexamer, respectively. The pH of the formulations was re-checked, and adjusted to 7.0, 7.1, 7.2, and 7.3, if necessary, using small volumes of sodium hydroxide. The formulation matrix is shown in Table 9.

TABLE 9

Formulations with Varying Zinc and pH

| pH | Zinc Content | | |
|---|---|---|---|
| 7.3 | 0.39% | 0.45% | 0.51% |
| 7.2 | 0.39% | 0.45% | 0.51% |
| 7.1 | 0.39% | 0.45% | 0.51% |
| 7.0 | 0.39% | 0.45% | 0.51% |

Procedure: Formulations were placed into refrigerated storage (2-8° C.; approx. 5° C.) and were stored for up to 25 weeks. Samples were taken time 0, 2 weeks, 5 weeks, 10 weeks, and 25 weeks in storage. The insulin concentration of the formulations (insulin solubility) was determined via ultra violet spectroscopy at 276 nm wavelength.

Figure 9:
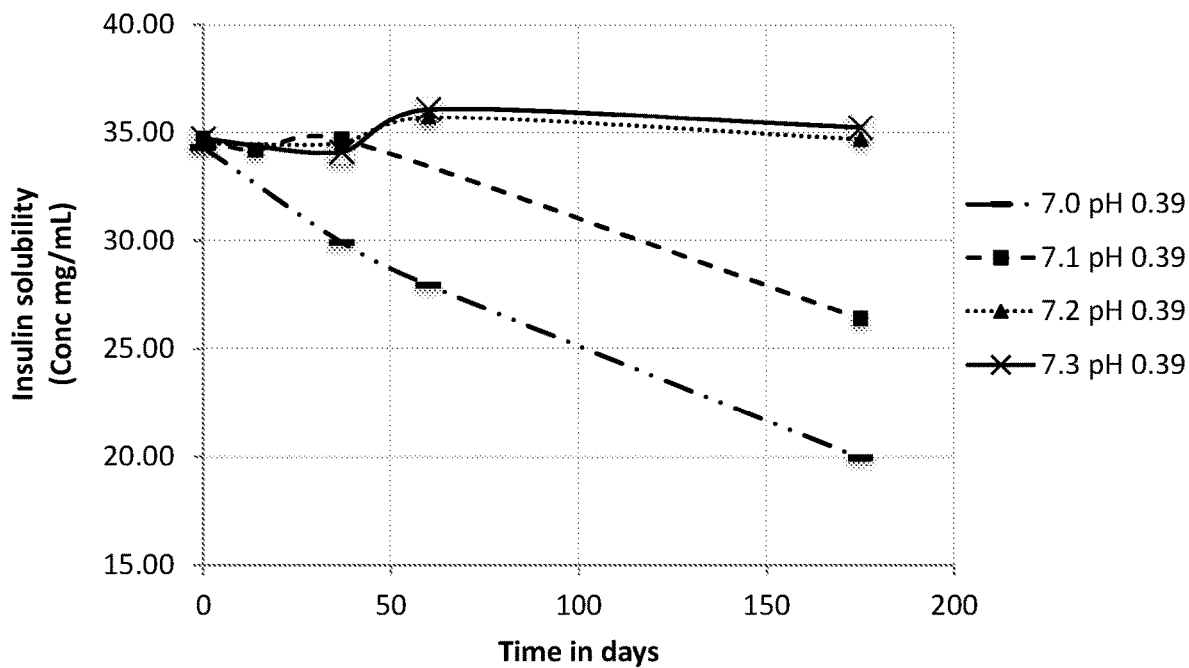
FIG. 9 shows the insulin solubility, measured by concentration change, in formulations containing 0.39% w/w zinc to insulin over time as a function of pH according to some aspects.
Figure 10:
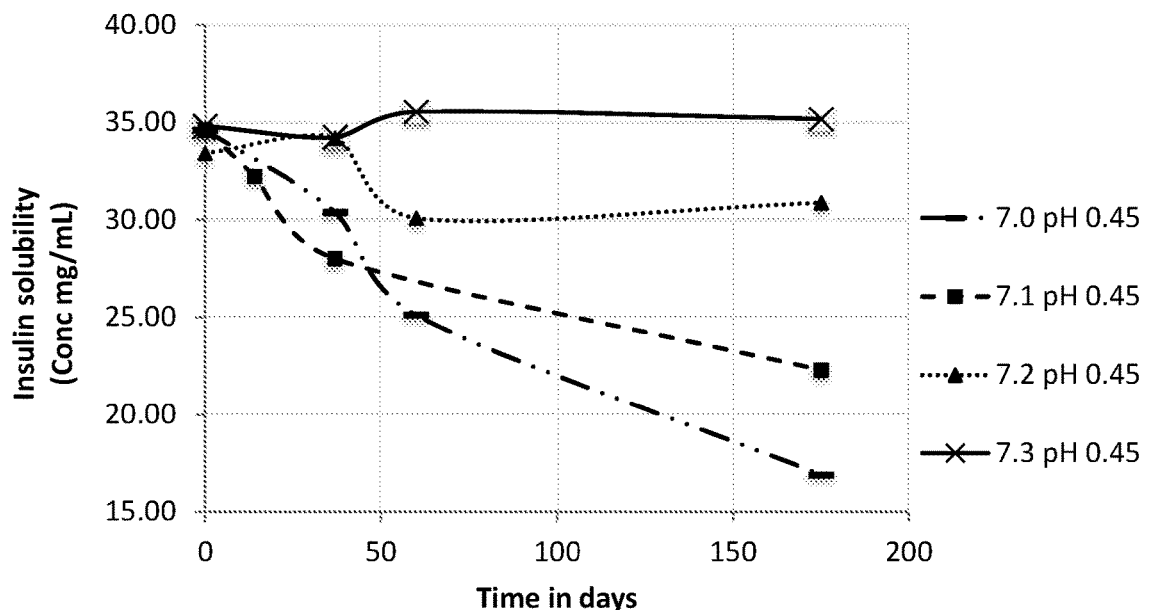
FIG. 10 shows the insulin concentration change, measured by concentration change, in formulations containing 0.45% w/w zinc to insulin over time as a function of pH according to some aspects.
Figure 11:
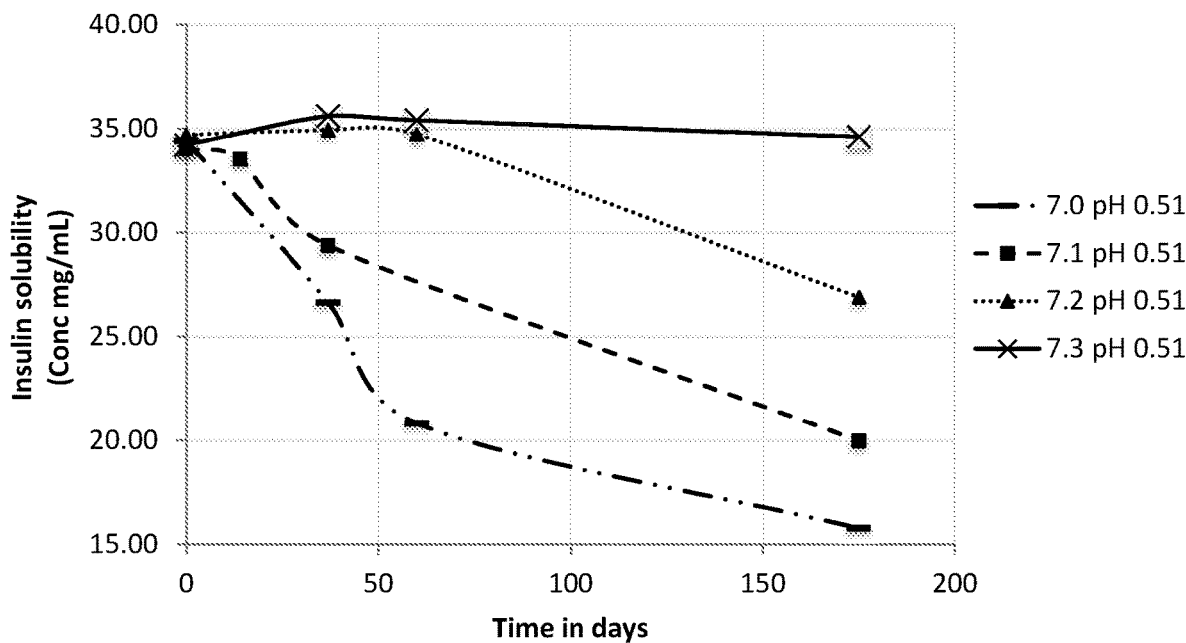
FIG. 11 shows the insulin concentration change, measured by concentration change, in formulations containing 0.51% w/w to insulin zinc over time as a function of pH according to some aspects.
Figure 12:
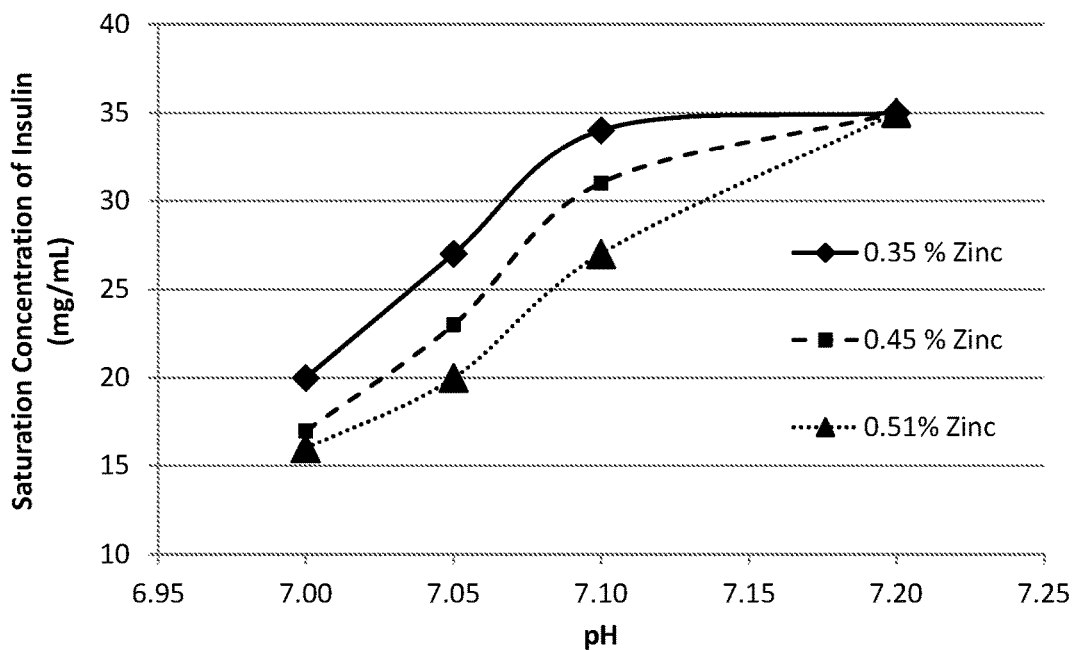
FIG. 12 shows a comparison of the final concentration of insulin in formulations containing 0.39% w/w, 0.45% w/w, and 0.51% w/w zinc to insulin as a function of pH and zinc concentration according to some aspects.
Figure 13:
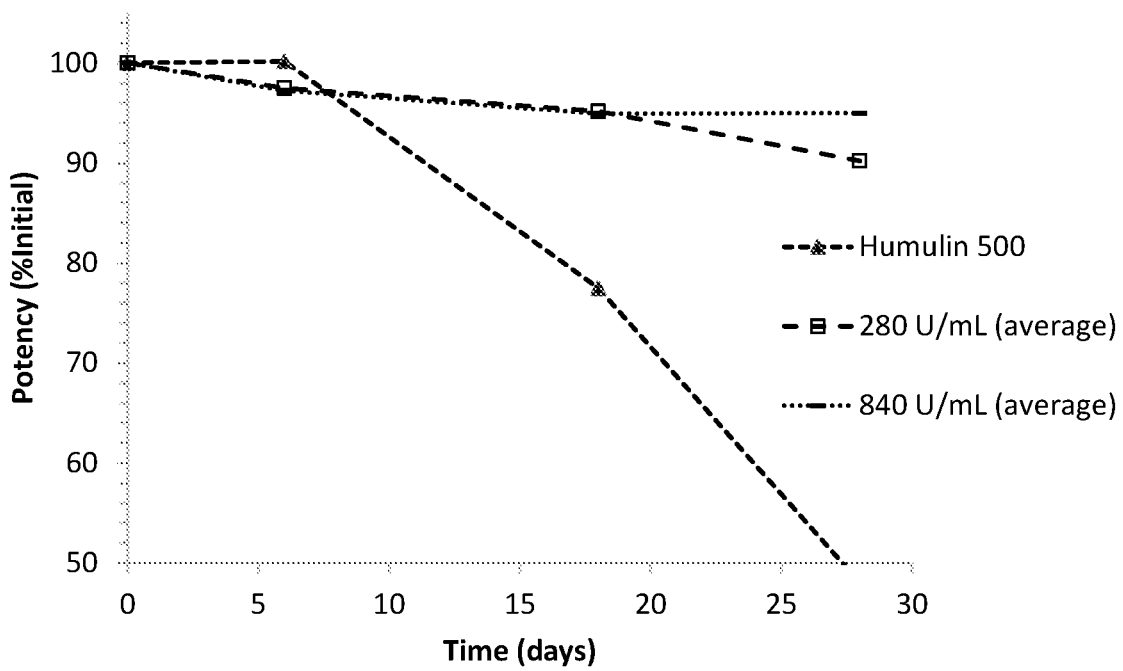
FIG. 13 shows a stability assessment following exposure to shear forces of preservative free formulations containing 280 U/mL and 840 U/mL insulin in comparison to commercial Humulin R® U-500, which contains a phenolic preservative, according to some aspects. The formulations were shaken over a period of 28 days. Insulin concentration was measured by HPLC, and potency is plotted as percent initial insulin concentration over time.

Results: The analytical results for this experiment are shown in FIGS. 9-12 and are described below. Specifically, FIGS. 9-11 show the insulin concentration change in the formulations over time as a function of pH, and FIG. 12 shows a comparison of the final concentration of insulin in each formulation as a function of pH and zinc concentration.

As shown in FIG. 9, the insulin concentration of the formulations remain the same within experimental error at pH 7.2 and 7.3 and 0.39% zinc content, but drop over time at pH 7.0 and 7.1 with 0.39% zinc content. Loss occurs gradually and cannot be observed at pH 7.1 until after the 8 week time point. The drop at pH 7.0 is 14.4 mg/mL, equating to an 41.9% loss. The drop at pH 7.1 is 8.3 mg/mL equating to a 23.9% loss.

As shown in FIG. 10, the insulin concentration of the formulations remain the same within experimental error at pH 7.3 and 0.45% zinc content, but drop over time at pH 7.0, 7.1 and 7.2 with 0.45% zinc content. Loss occurs gradually and cannot be observed at pH 7.2 until after the 8 week time point. The drop at pH 7.0 is 17.7 mg/mL, equating to an 51.2% loss. The drop at pH 7.1 is 12.3 mg/mL equating to a 35.6% loss. The drop at pH 7.2 is 2.5 mg/mL equating to a 7.6% loss.

As shown in FIG. 11, the insulin concentration of the formulations remain the same within experimental error at pH 7.3 and 0.51% zinc content, but drop over time at pH 7.0, 7.1 and 7.2 with 0.51% zinc content. Loss occurs gradually and cannot be observed at pH 7.2 until after the 8 week time point. The drop at pH 7.0 is 18.6 mg/mL, equating to an 54.1% loss. The drop at pH 7.1 is 14.0 mg/mL equating to a 41.2% loss. The drop at pH 7.2 is 7.8 mg/mL equating to a 22.5% loss.

FIG. 12 illustrates the insulin concentration of the formulations at the 25 week time point as an overall function of zinc content and pH. The results show a trend towards greater solubility at higher pH and lower zinc concentration. All solutions were fully soluble at pH 7.3. In general, above pH 7.3 (for example, at pH 7.3-7.8), insulin easily remained soluble at 35 mg/mL at zinc concentrations of 0.51% w/w relative to insulin. However, as noted in Example 1, zinc concentrations of 0.61% w/w relative to insulin showed precipitation at pH 7.5.

The results of this study indicate a complex relationship between pH, zinc concentration, and the physical stability of insulin formulations over time. Because of the time dependent relationship between pH, zinc concentration and solubility, it is important to assess insulin formulations for long term stability comparable to anticipated shelf life expectations or requirements. The results of this study indicate that, in addition to pH, the concentration of zinc in insulin formulations is a critical component for long term physical stability.

Example 5

Purpose: To establish the physical stability of provided insulin formulations exposed to shaking. Shaking simulates conditions during shipment and handling of insulin formulations, which can lead to fibrillation. Insulin formulations having different buffer were compared to a commercially available insulin formulation containing metacresol as a stabilizer/preservative and glycerin.

Formulation Components: Formulations were made using USP recombinant human insulin (Sanofi-Aventis, Material: 192228, GMID: 341921), which contained 0.50% w/w zinc to insulin (about 2.6 zinc per six insulin monomers). The following materials were obtained from JT Baker: USP sodium citrate dihydrate; HPLC grade water; hydrochloric acid (37%), and sodium hydroxide pellets.

Method Description: The formulations were prepared containing 29.2 mg/mL (840 U/mL, 5.03 mM) and 9.7 mg/mL (280 U/mL, 1.67 mM) insulin in 6 mM sodium citrate and 70 mM sodium chloride. Recombinant human insulin was weighed and dissolved to 80% of final volume in 87.5 mM hydrochloric acid. Sodium citrate dihydrate was added to the formulation to a concentration of 0, 3, 6, 12, and 24 mM concentration (relative to the final dilution volume). Sodium hydroxide (1M) was added to adjust the pH to 7.55. The formulations were adjusted to final volume with water and the pH was rechecked. For ease of reference, these formulations will be referred to as preservative free formulations.

Preservative free formulations were compared to commercial insulin formulation Humulin R® U-500 (HI-500) (NDC 0002-8501-01) containing 500 U/mL (17.4 mg/mL) insulin, 0.017 mg zinc/100 insulin units (equivalent to 0.49% zinc, or about 2.6 zinc per insulin hexamer), 16 mg/mL (1.6%) glycerin, and 2.5 mg/mL (0.25%) meta-cresol, with HCl and/or NaOH added for pH adjustment. Humulin, Lot No. C398930A, EXP: 10/2016 was purchased from Eli Lilly and Company. This formulation is referred to as "Humulin" below.

Procedure: 10 mL of each formulation was aliquotted into 20 mL Trace Clean (VWR Part #159000-020) scintillation vials. Vials were secured to an orbital shaker and shaken at 120 RPM (120 revolutions per minute with an orbital diameter of 18 mm). Samples were analyzed at time points from 0-28 days or 0-15 days using two orthogonal methods designed to assess the concentration of insoluble insulin fibrils (aggregated insulin).

1. Potency by HPLC
   Potency is a measurement of insulin concentration. As insulin fibrillates and precipitates, the potency of insulin in solution decreases. Lower potency correlates to greater aggregation (physical instability). Assessments were made at time 0, day 6, day 18, and day 28.
2. Turbidity by Nephelometer
   Turbidity is a measurement of the cloudiness or haziness of a solution. For the purpose of this analysis, turbidity describes the presence of insoluble particulate (insulin fibrils) having precipitated from sample solutions. Higher turbidity correlates to greater aggregation (physical instability). Assessments were made a time 0, day 4, day 6, day 8, day 11, and day 15.

Results: The analytical results for this experiment are shown in Tables 10-11 and FIG. 13 and FIG. 14 and are described below.

TABLE 10

Potency of Shaken Insulin Formulations

| | | Insulin Concentration (mg/mL) | | | |
|---|---|---|---|---|---|
| Sample | | 0 | 6 days | 18 days | 28 days |
| Humulin (500 U/mL) | | 17.1 | 17.1 | 13.2 | 8.2 |
| 9.7 mg/mL | 0 mM Citrate | NS[1] | 9.7 | 9.3 | 8.7 |
| Insulin | 3 mM Citrate | NS[1] | NS[2] | 9.7 | 9.1 |
| | 6 mM Citrate | 10.0 | 9.6 | 9.4 | 9.0 |
| | 12 mM Citrate | NS[1] | 9.8 | 9.7 | 9.5 |
| | 24 mM Citrate | NS[1] | 9.8 | 9.4 | 8.7 |

TABLE 10-continued

Potency of Shaken Insulin Formulations

| Sample | | Insulin Concentration (mg/mL) | | | |
|---|---|---|---|---|---|
| | | 0 | 6 days | 18 days | 28 days |
| 29.2 mg/mL Insulin | 0 mM Citrate | NS[1] | 29.0 | 28.3 | 28.3 |
| | 3 mM Citrate | NS[1] | 28.7 | 28.1 | 28.2 |
| | 6 mM Citrate | 29.6 | 28.9 | 28.3 | 28.1 |
| | 12 mM Citrate | NS[1] | 28.8 | 27.7 | 28.2 |
| | 24 mM Citrate | NS[1] | 28.6 | 28.1 | 27.9 |

[1]Not Sampled. Assumed to be equivalent for formulations at each concentration at T = 0.
[2]Not Sampled. Data was not available for this sample at this time point.

TABLE 11

Turbidity of Shaken Insulin Formulations

| Sample | | Turbidity (NTU) | | | | | |
|---|---|---|---|---|---|---|---|
| | | 0 | 4 days | 6 days | 8 days | 11 days | 15 days |
| Humulin (500 U/mL) | | 2 | 42 | 129 | >200[2] | >200[2] | >200[2] |
| 9.7 mg/mL Insulin | 0 mM Citrate | N/A[1] | 2 | 7 | 26 | 52 | 86 |
| | 3 mM Citrate | N/A[1] | 2 | 2 | 3 | 23 | 30 |
| | 6 mM Citrate | 2 | 2 | 9 | 53 | 74 | 109 |
| | 12 mM Citrate | N/A[1] | 2 | 2 | 2 | 2 | 3 |
| | 24 mM Citrate | N/A[1] | 2 | 2 | 62 | 86 | 124 |
| 29.2 mg/mL Insulin | 0 mM Citrate | N/A[1] | 12 | 46 | 82 | 101 | 172 |
| | 3 mM Citrate | N/A[1] | 18 | 79 | 122 | 151 | 173 |
| | 6 mM Citrate | 5 | 13 | 89 | 129 | 168 | 188 |
| | 12 mM Citrate | N/A[1] | 4 | 51 | 103 | 145 | 166 |
| | 24 mM Citrate | N/A[1] | 6 | 84 | 129 | 141 | 174 |

[1]Not Applicable. Assumed to be equivalent for samples at each concentration at T = 0.
[2]Turbidity was >200; above threshold for accurate measurement.

The preservative free insulin formulations were found to have increased resistance to fibrillation (shear force) compared to the commercial Humulin formulation, as described further below.

Formulations described herein showed potencies of 8.7-9.5 mg/mL and 27.9-28.3 mg/mL after 28 days for 280 U/mL and 840 U/mL concentrations, respectively, compared to starting concentrations of 10.0 and 29.6 mg/mL. This amounts to a cumulative loss due to fibrillation of approximately 0.5-1.7 mg/mL.

Humulin showed a potency of 8.2 mg/mL after 28 days, compared to a starting potency of 17.1 mg/mL. This amounted to a cumulative loss due to fibrillation of 8.9 mg/mL.

This data demonstrates that the commercial Humulin formulation experienced a cumulative loss in potency of 4-18 fold greater than that of the preservative free formulations described herein.

The Humulin formulation showed an increase in turbidity (presence of insoluble fibrils) as early as day 4, with readings above the measurable range of the device by day 8. In contrast, the preservative free formulations described herein did not show significant increases in turbidity until days 6 or 8, with measurements still within range at day 15.

This study indicates that formulations described herein have substantial resistance to fibrillation and, further, are more resistant than commercial formulations having the stabilizing effect of a phenolic preservative.

Example 6

The purpose of this study was to evaluate whether phenol affects the solubility of insulin in insulin formulations having a very high concentration of insulin. The study evaluated the physical stability of preservative free insulin formulations according to this disclosure relative to insulin formulations containing a phenolic preservative/stabilizer, both formulations containing saturating levels of insulin (70 mg/mL, 12 mM, 2016 U/mL). The phenol-containing formulation included 0.25% wt/vol phenol, which is the concentration found in common commercial formulations (such as, for example, Humulin® R 500; see Example 5). While phenol is added to Humulin® on a wt/wt basis, the phenol-containing formulations assessed in the following experiments included phenol on a wt/vol basis. Wt/wt and wt/vol are essentially interchangeable in this context because the density of Humulin® and the phenol-containing formulations is very close to 1 g/mL.

Formulation Components: The formulations were made using USP recombinant human insulin (Sanofi-Aventis, Material: 192228, GMID: 341921), which contained 0.50% wt/wt zinc to insulin (about 2.6 zinc per six insulin monomers). The following materials were obtained from JT Baker: USP sodium citrate dihydrate; USP grade phenol; HPLC grade water; hydrochloric acid (37%), and sodium hydroxide pellets.

1. Bulk Formulation:
   A bulk formulation was prepared and was later separated into four aliquots. Recombinant human insulin was weighed and dissolved to 80% of final volume in 87.5 mM hydrochloric acid. Sodium citrate dihydrate was added to the formulation to a final concentration 6 mM. Aliquots of the bulk were removed to prepare preservative free and preserved formulations, as described below. After these final additions, the insulin concentration was 70 mg/mL. This formulation was intended to be a saturated solution such that an insulin concentration of 70 mg/mL is near the limit of insulin solubility at the pH values evaluated. Final concentration of NaCl of 70 mM.

2. Preservative Free Formulations:
   Two aliquots were removed from the bulk formulation. Sodium hydroxide (1M) was added to adjust the pH to 7.20 and 7.40, respectively. The formulations were adjusted to final volume with water and the pH was rechecked. Final concentration of NaCl of 70 mM.

3. Phenolic Formulations:
   Two aliquots were removed from the bulk formulation. Phenol was added at a concentration of 0.25% wt of final volume. Sodium hydroxide (1M) was added to adjust the pH to 7.20 and 7.40, respectively. The formulations were adjusted to final volume with water and the pH was rechecked.

Procedure: 20 mL of each formulation was placed at 5° C. and analyzed for insulin potency at time points of 0, 3 months, and 6 months. Samples were prepared by centrifuging an aliquot of formulation (approximately 300 µL) to remove insoluble protein precipitates. The supernatant was evaluated by HPLC for potency (reported as concentration in mg/mL) as described in Example 3.

Results: The analytical results for this experiment are shown in Table 12 and FIG. 15 and are described below.

TABLE 12

Potency (Concentration) of Preservative Free and Preserved Formulations

| Sample | Concentration (mg/mL) (% Original) | | |
|---|---|---|---|
| | 0 mo* | 3 mo | 6 mo |
| Phenol, 0.25%, pH 7.2 | 59.21 (84.6%) | 23.1 (33.0%) | 23.6 (33.7%) |
| Phenol, 0.25%, pH 7.4 | 66.41 (94.9%) | 33.91 (48.4%) | 33.7 (48.1%) |
| Preservative Free, pH 7.2 | 69.31 (99.0%) | 68.11 (97.3%) | 65.2 (93.1%) |
| Preservative Free, pH 7.4 | 68.41 (97.7%) | 67.51 (96.4%) | 69.4 (99.1%) |

Formulations containing phenol showed immediate precipitation, bringing their concentrations below 70 mg/mL at initial analysis and lost over half of their potency by 3 months. After 6 months, the phenol containg formulations showed potencies of 33.7% and 48.1% of their theoretical potency at pH 7.2 and 7.4, respectively. In contrast, the preservative free formulations experienced a small potency loss between 3 and 6 months of storage for the pH 7.2 formulation, while the pH 7.4 formulation maintained its potency over the course of the study. At 6 months, the potency of the preservative free formulations was 93.1% and 99.1% for the preservative-free formulations at pH 7.2 and 7.4, respectively.

The high concentration preservative-free insulin formulations thus showed increased physical stability (solubility) compared to phenol containing formulations. This result is surprising because, as discussed above, preservatives are generally added to enhance the chemical stability of injectable insulin formulations. Importantly, the decrease in potency was observed with extended analysis. Saturated solubility studies are sometimes performed using short time courses (often less than one day). If this study had not extended to longer time points, the extent of the loss of potency would not have been observed for the phenol containing formulations.

Achieving high insulin concentration with acceptable physical stability is important for inhalable insulin inhalation solutions and, as such, the preservative free formulations of this disclosure appear to present an advantage towards this end.

It is understood that the numerical values set forth in this disclosure may include a degree of variability within reasonable experimental error. For example, the recited values may encompass values 10% above or below the recited value. In some instances, the variability accounts for transitioning between the units used to refer to the feature (such as, for example, converting between mg/mL and U/mL). In some instances, this variability is indicated by use of the term "about" but it is implied in all values relating to the features of the formulations and other aspects of this disclosure regardless of whether the value is modified by the term "about".

The foregoing description of certain embodiments, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure. Certain features that are described in this specification in the context of separate embodiments can also be implemented in combination in a single implementation. Conversely, various features that are described in the context of a single implementation can also be implemented in multiple ways separately or in any suitable subcombination. Moreover, although features may be described above as acting in certain combinations, one or more features from a combination can in some cases be excised from the combination, and the combination may be directed to a subcombination or variation of a subcombination. Thus, particular embodiments have been described. Other embodiments are within the scope of the disclosure.

All printed patents and publications referred to in this application are hereby incorporated herein in their entirety by this reference.

What is claimed is:

1. A method of treating a subject with diabetes mellitus, comprising administering to a subject having diabetes mellitus a therapeutically effective amount of an insulin formulation, comprising:
   insulin at a minimal concentration of 1-13 mM;
   a salt at a concentration of 50-150 mM;
   a pH buffering agent at a concentration of 3-24 mM, wherein the pH buffering agent comprises citrate;
   zinc at a ratio of 1.9-2.7 zinc ions per insulin hexamer; and
   a pH in the range of 7.2 to 8.0,
   wherein the formulation does not contain preservatives or stabilizers, and
   wherein the formulation is administered to the subject via injection.

2. The method of claim 1, wherein the insulin is human insulin.

3. The method of claim 1, wherein the formulation comprises at least 30 mg/mL insulin.

4. The method of claim 1, wherein the formulation comprises 10-30 mg/mL insulin.

5. The method of claim 1, wherein the insulin concentration is about 30 mg/mL and the pH is about 7.55.

6. The method of claim 1, wherein the salt is a chloride salt.

7. The method of claim 1, wherein the salt is NaCl.

8. The method of claim 1, wherein the tonicity (ionic strength) of the formulation is 100-300 mOsm.

9. The method of claim 1, wherein the formulation does not contain surfactants.

10. The method of claim 1, wherein the formulation is administered to the subject intravenously, intramuscularly, or intraperitoneally.

11. The method of claim 1, wherein the therapeutically effective amount of the formulation is 2 U to 28 U delivered via subcutaneous injection.

12. The method of claim 1, wherein the formulation is administered to the subject at least once a day.

13. The method of claim 1, wherein the formulation is administered to the subject at least 15 minutes before the subject eats a meal.

14. The method of claim 1, wherein the formulation is administered to the subject just prior to the subject eating a meal.

* * * * *

UNITED STATES PATENT AND TRADEMARK OFFICE
CERTIFICATE OF CORRECTION

PATENT NO. : 11,096,990 B2  
APPLICATION NO. : 16/168186  
DATED : August 24, 2021  
INVENTOR(S) : Blaine Bueche et al.

Page 1 of 1

It is certified that error appears in the above-identified patent and that said Letters Patent is hereby corrected as shown below:

On the Title Page

Item (73) Assignee:
Delete "Brisbane, CA" and Insert -- Durham, NC --, therefor.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*